US011782957B2

(12) United States Patent
Roberts et al.

(10) Patent No.: US 11,782,957 B2
(45) Date of Patent: Oct. 10, 2023

(54) SYSTEMS AND METHODS FOR AUTOMATED CLASSIFICATION OF A DOCUMENT

(71) Applicant: GRAIL, LLC, Menlo Park, CA (US)

(72) Inventors: Kathan Roberts, Palo Alto, CA (US); Max Weiland Rosen, San Francisco, CA (US); Joerg Bredno, San Francisco, CA (US); Jafi Lipson, Palo Alto, CA (US); Harit Nandani, San Carlos, CA (US)

(73) Assignee: GRAIL, LLC, Menlo Park, CA (US)

( * ) Notice: Subject to any disclaimer, the term of this patent is extended or adjusted under 35 U.S.C. 154(b) by 79 days.

(21) Appl. No.: 17/714,826

(22) Filed: Apr. 6, 2022

(65) Prior Publication Data
US 2022/0327145 A1 Oct. 13, 2022

Related U.S. Application Data

(60) Provisional application No. 63/172,471, filed on Apr. 8, 2021, provisional application No. 63/248,755, filed on Sep. 27, 2021.

(51) Int. Cl.
G06F 17/00 (2019.01)
G06F 16/28 (2019.01)
(Continued)

(52) U.S. Cl.
CPC ........... *G06F 16/285* (2019.01); *G06N 20/00* (2019.01); *G06V 30/19173* (2022.01); *G16H 15/00* (2018.01)

(58) Field of Classification Search
CPC ....... G06F 16/285; G06F 16/35; G06N 20/00; G06V 30/19173; G06V 30/412;
(Continued)

(56) References Cited

U.S. PATENT DOCUMENTS 6,502,081 B1 12/2002 Wiltshire et al.
2005/0108001 A1 5/2005 Aarskog
(Continued)

FOREIGN PATENT DOCUMENTS

WO WO 2021/252419 A1 12/2021

OTHER PUBLICATIONS

Gao et al., Using Natural Language Processing to Extract Mammography Findings, Journal of Biomedical Informatics, vol. 54, Apr. 2015.
(Continued)

Primary Examiner — Greta L Robinson
(74) Attorney, Agent, or Firm — Bookoff McAndrews, PLLC

(57) ABSTRACT

A method for extracting information from a dataset, e.g., a document, includes: receiving the dataset at an information handling device, optionally, extracting, via optical character recognition implemented by a processor of the information handling device, textual information associated with the dataset, and classifying the dataset into one of a plurality of classes. Classifying the dataset may include computing a similarity score for each of the plurality of classes for each of a plurality of window regions of the dataset, calculating a subset of highest similarity scores for each of the plurality of classes for each of the plurality of window regions, determining overall similarity scores for each of the plurality of classes, and classifying the dataset as corresponding to a class with a highest overall similarity score.

24 Claims, 9 Drawing Sheets

(51) Int. Cl.
*G06V 30/19* (2022.01)
*G06N 20/00* (2019.01)
*G16H 15/00* (2018.01)

(58) Field of Classification Search
CPC ........ G16H 50/20; G16H 50/70; G16H 15/00; G16H 20/00; G16H 30/40
See application file for complete search history.

(56) References Cited

U.S. PATENT DOCUMENTS

| | | | |
|---|---|---|---|
| 2006/0010145 | A1 | 1/2006 | Al-Kofahi et al. |
| 2019/0148019 | A1* | 5/2019 | Bundschus ............ A61P 43/00 705/2 |
| 2019/0354584 | A1* | 11/2019 | Wallenfelt ............ G06F 40/131 |
| 2020/0097545 | A1* | 3/2020 | Chatterjee ............... G06F 40/30 |
| 2020/0125574 | A1 | 4/2020 | Ghoshal et al. |
| 2020/0334809 | A1 | 10/2020 | Vianu et al. |
| 2020/0349199 | A1 | 11/2020 | Jayaraman |
| 2021/0090694 | A1* | 3/2021 | Colley ................... G16H 50/70 |
| 2022/0108108 | A1* | 4/2022 | Sathi .................... G06V 30/414 |

OTHER PUBLICATIONS

Savova et al., Use of Natural Language Processing to Extract Clinical Cancer Phenotypes from Electronic Medical Records, Cancer Research Online, American Association of Cancer Research, Aug. 8, 2019.

Percha et al., Automatic Classification of Mammography Reports by BI-RADS Breast Tissue Composition Class, Journal of the American Medical Informatics Association, vol. 19, 2012.

Castro et al., Automated Annotation and Classification of BI-RADS Assessment from Radiology Reports, Journal of Biomedical Informatics, vol. 69, 2017.

Bozkurt et al., Automatic Abstraction of Imaging Observations with their Characteristics from Mammography Reports, Journal of the American Medical Informatics Association, 2015.

Banerjee et al., Automatic Inference of BI-RADS Final Assessment Categories from Narrative Mammography Report Findings, Journal of Biomedical Informatics, vol. 92, 2019.

Manning, Christopher D., et al. Introduction to Information Retrieval, Cambridge University Press, 2008, https://nlp.stanford.edu/IR-book/.

International Search Report and Written Opinion issued in PCT/US2022/023913 dated Jul. 28, 2022 (10 pages).

Park et al., "Implementation of an efficient requirements-analysis supporting system using similarity measure techniques" Information and Software Technology 42 (2000) 429-438; vol. 42, Issue 6, Apr. 15, 2000, pp. 429-438; (Oct. 4, 2000); retrieved on [Jul. 7, 2022], retrieved from the internet <URL: https://www.sciencedirect.com/science/article/pii/S0950584999001020/pdfft?md5=8996a5f6d9ef813a803d 142fcf14311d&pid=1-s2.0-S0950584999001020-main.pdf>.

* cited by examiner

SYSTEMS AND METHODS FOR AUTOMATED CLASSIFICATION OF A DOCUMENT

CROSS-REFERENCE TO RELATED APPLICATIONS

This application claims the benefit of priority from U.S. Provisional Patent Application No. 63/172,471, filed Apr. 8, 2021, and U.S. Provisional Patent Application No. 63/248,755, filed Sep. 27, 2021, each of which is hereby incorporated by reference herein in its entirety.

TECHNICAL FIELD

Various embodiments of this disclosure relate generally to machine-learning based techniques for automatically extracting information from a dataset, for example, a document containing text. The dataset or document may be in a variety of formats, for example, portable document format (PDF), plain text format, or virtually any other structured or unstructured format type. In some embodiments, the disclosure relates to systems and methods for automatically extracting medical information from medical reports, and, in some embodiments, the disclosure relates to systems and methods for automatically extracting breast density information from mammogram reports.

BACKGROUND

Many documents do not reliably include information in a format that a computer system can easily parse. For example, extracting information from textual documents that do not have standard structures or fields may be challenging for a computer system. Conventional language analysis techniques may have trouble automatically extracting information from textual documents that lack specific structures or fields, or for which the information is not provided in standardized language. This may make it difficult for a computer system to efficiently analyze and classify multiple documents efficiently, e.g., when aggregating or analyzing data.

This may be particularly true in the medical community, where textual documents, e.g., medical reports, may be formatted differently by different physicians, practices, electronic medical systems, etc. For example, medical reports may not contain fields for every condition, test type, test result, patient attribute, etc., and, even if the documents were formatted uniformly, the language used to describe different patients' conditions may vary across the same diagnosis or image read.

As an example, breast density is a risk factor for breast cancer and is a standard metric in most mammography screening cohorts. Yet breast imaging reports may not contain structured breast density fields. Instead, the breast imaging reports may provide only a human-readable, free text report with information about the mammogram that may include breast density. There is a need for an automated process for extracting breast density information to analyze multiple documents efficiently, for example, when aggregating data for studies.

This disclosure is directed to addressing one or more of the above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, methods and systems are disclosed for automatically extracting information from a document.

A computer-implemented method for extracting information from a document, comprising receiving the document, the document containing textual information, and classifying the document into one of a plurality of classes. The classifying further comprising computing a similarity score for each of the plurality of classes for each of a plurality of window regions of the document, determining, based on a subset of highest similarity scores computed for each of the plurality of classes for each of the plurality of window regions, overall similarity scores for each of the plurality of classes for the document, and classifying the document as corresponding to a class of the plurality of classes with a highest overall similarity score for the document. The computing further comprising sliding a window across the textual information to define the plurality of window regions, and for each of the plurality of window regions: computing a relevance metric for the window region, and calculating the similarity score for each of the plurality of classes by calculating a similarity function between the relevance metric for the window region and an average relevance metric for each of the plurality of classes.

A computer system for extracting information from a document, the computer system comprising at least one memory storing instructions, and at least one processor configured to execute the instructions to perform operations comprising accessing the at least one memory and execute processor-readable instructions, which when executed by the at least one processor configures the at least one processor to perform a plurality of functions. The plurality of functions include receiving the document, the document containing textual information, and classifying the document into one of a plurality of classes. The classifying further comprises computing a similarity score for each of the plurality of classes for each of a plurality of window regions of the document, determining, based on a subset of highest similarity scores computed for each of the plurality of classes for each of the plurality of window regions, overall similarity scores for each of the plurality of classes for the document, and classifying the document as corresponding to a class of the plurality of classes with a highest overall similarity score for the document. The computing further comprises sliding a window across the textual information to define the plurality of window regions, and for each of the plurality of window regions: computing a relevance metric for the window region, and calculating the similarity score for each of the plurality of classes by calculating a similarity function between the relevance metric for the window region and an average relevance metric for each of the plurality of classes.

A non-transitory computer-readable medium storing instructions that, when executed by a processor, cause the processor to perform operations for extracting information from a document, the operations comprising receiving the document, the document containing textual information, and classifying the document into one of a plurality of classes. The classifying further comprises computing a similarity score for each of the plurality of classes for each of a plurality of window regions of the document, determining, based on a subset of highest similarity scores computed for each of the plurality of classes for each of the plurality of window regions, overall similarity scores for each of the plurality of classes for the document, and classifying the document as corresponding to a class of the plurality of classes with a highest overall similarity score for the document. The computing further comprises sliding a window across the textual information to define the plurality of window regions, and for each of the plurality of window regions: computing a relevance metric for the window region, and calculating the similarity score for each of the plurality of classes by calculating a similarity function between the relevance metric for the window region and an average relevance metric for each of the plurality of classes.

A computer-implemented method for extracting information from a document, comprising receiving the document, the document containing textual information, and classifying the document into one of a plurality of classes. The classifying further comprising computing a similarity score for each of the plurality of classes for each of a plurality of window regions of the document, wherein the computing includes sliding a window across the textual information to define the plurality of window regions, determining, based on a subset of highest similarity scores, overall similarity scores for each of the plurality of classes for the document, and classifying the document as corresponding to a class of the plurality of classes with a highest overall similarity score for the document.

A computer-implemented method for extracting information from a dataset, including: receiving, at an information handling device, a dataset; extracting, via optical character recognition implemented by a processor of the information handling device, textual information associated with the dataset; and classifying the dataset into one of a plurality of classes, the classifying further comprising: computing a similarity score for each of the plurality of classes for each of a plurality of window regions of the dataset, the computing further comprising: sliding a window across the textual information to define the plurality of window regions, and for each of the plurality of window regions: computing a relevance metric for the window region; and calculating the similarity score for each of the plurality of classes by calculating a similarity function between the relevance metric for the window region and an average relevance metric for each of the plurality of classes; determining, based on a subset of highest similarity scores computed for each of the plurality of classes for each of the plurality of window regions, overall similarity scores for each of the plurality of classes for the dataset; and classifying the dataset as corresponding to a class of the plurality of classes with a highest overall similarity score for the dataset.

A computer system for extracting information from a dataset, the computer system including: at least one memory storing instructions; and at least one processor configured to execute the instructions to perform operations comprising: access the at least one memory and execute processor-readable instructions, which when executed by the at least one processor configures the at least one processor to perform a plurality of functions, including functions for: receiving, at an information handling device associated with the computer system, the dataset; extracting, via optical character recognition implemented by the at least one processor, textual information associated with the dataset; and classifying the dataset into one of a plurality of classes, the classifying further comprising: computing a similarity score for each of the plurality of classes for each of a plurality of window regions of the dataset, the computing further comprising: sliding a window across the textual information to define the plurality of window regions, and for each of the plurality of window regions: computing a relevance metric for the window region; and calculating the similarity score for each of the plurality of classes by calculating a similarity function between the relevance metric for the window region and an average relevance metric for each of the plurality of classes; determining, based on a subset of highest similarity scores computed for each of the plurality of classes for each of the plurality of window regions, overall similarity scores for each of the plurality of classes for the dataset; and classifying the dataset as corresponding to a class of the plurality of classes with a highest overall similarity score for the dataset.

A non-transitory computer-readable medium storing instructions that, when executed by a processor, cause the processor to perform operations for extracting information from a dataset, the operations including: receiving the dataset; extracting, via optical character recognition, textual information associated with the dataset; and classifying the dataset into one of a plurality of classes, the classifying further comprising: computing a similarity score for each of the plurality of classes for each of a plurality of window regions of the dataset, the computing further comprising: sliding a window across the textual information to define the plurality of window regions, and for each of the plurality of window regions: computing a relevance metric for the window region; and calculating the similarity score for each of the plurality of classes by calculating a similarity function between the relevance metric for the window region and an average relevance metric for each of the plurality of classes; determining, based on a subset of highest similarity scores computed for each of the plurality of classes for each of the plurality of window regions, overall similarity scores for each of the plurality of classes for the dataset; and classifying the dataset as corresponding to a class of the plurality of classes with a highest overall similarity score for the dataset.

A computer-implemented method for extracting information from a dataset, including: receiving, at an information handling device, the dataset; extracting, via optical character recognition implemented by a processor of the information handling device, textual information associated with the dataset; and classifying the dataset into one of a plurality of classes, the classifying further comprising: computing a similarity score for each of the plurality of classes for each of a plurality of window regions of the dataset, wherein the computing includes sliding a window across the textual information to define the plurality of window regions; determining, based on a subset of highest similarity scores, overall similarity scores for each of the plurality of classes for the dataset; and classifying the dataset as corresponding to a class of the plurality of classes with a highest overall similarity score for the dataset It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DETAILED DESCRIPTION OF EMBODIMENTS

Figure 1:
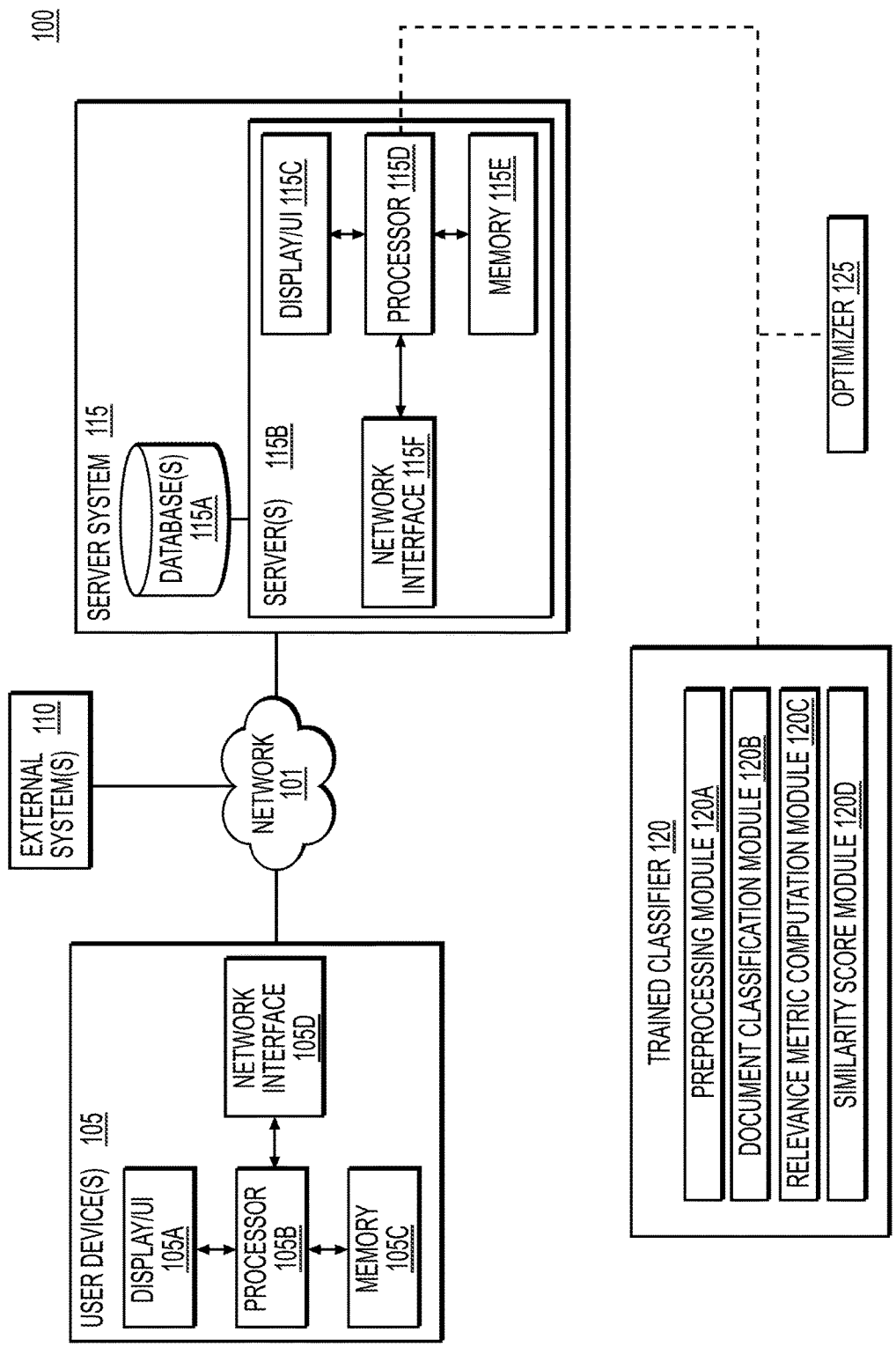
FIG. 1 depicts an exemplary environment for training a machine-learning model to automatically extract textual information from a document, according to one or more embodiments.

According to certain aspects of the disclosure, methods and systems are disclosed for automatically extracting information from a dataset, for example, a document, e.g., medical information from a medical report, such as a radiology report, and, in some embodiments, breast density information from a breast imaging report, and then classifying the document based on the extracted information.

Extracting information from unstructured datasets, e.g., documents, may be challenging. Conventional techniques may not be suitable, because such techniques are inefficient and may be dependent upon a document including particular fields, a particular structure, or consistent language used to describe the relevant information. Accordingly, improvements in technology relating to automatically extracting information from a document are needed.

The present disclosure can provide a system for automatically extracting textual information from a dataset, e.g., document, by incorporating a relevance metric analysis with a sliding-window structure. More specifically, the system can utilize machine learning (or any mathematical or statistical model) to search for targeted sections of a document that contain relevant information. Such a system may be quick to train and quick to execute, while still maintaining accuracy. The system may allow for the efficient processing of a large volume of documents.

As will be discussed in more detail below, in various embodiments, systems and methods are described for using machine learning to extract information from a dataset, e.g., document. By training a machine-learning model, e.g., via supervised or semi-supervised learning, to learn associations between document data and classification data, the trained machine-learning model may be usable to automatically extract information from a document.

Reference to any particular activity is provided in this disclosure only for convenience and is not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially," "about," and "generally," are used to indicate a possible variation of ±10% of a stated or understood value.

As used herein, the term "user" generally encompasses any person or entity that may receive information, resolution of an issue, purchase of a product, or engage in any other type of interaction with a provider. The term "browser extension" may be used interchangeably with other terms like "program," "electronic application," or the like, and generally encompasses software that is configured to interact with, modify, override, supplement, or operate in conjunction with other software.

As used herein, the term "information handling device" generally encompasses virtually any type of electronic computing device including, for example, laptop and/or personal computers, smart phones, tablet devices, wearable devices, hybrid devices, other types of user devices, and the like. The term "information handling device" may be used interchangeably with, or in place of, any or all of the aforementioned types of computing devices. Additionally, utilization of one of the foregoing terms over another may not be intended to be limiting unless explicitly designated as such.

As used herein, the term "dataset" generally encompasses any collection of data. For example, a dataset may be a document, e.g., a file containing text, images, tables, graphs, charts, any combination of the foregoing, etc., that may be presented in one or more different file formats (e.g., portable document format (PDF), plain text format, virtually any other structured or unstructured format type, etc.). The terms "dataset" and "document" may be used interchangeably herein and the utilization of one term over another is not intended to be limiting unless explicitly designated as such.

As used herein, a "machine-learning model" or "trained classifier" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

The execution of the machine-learning model may include deployment of one or more machine-learning techniques, such as k-nearest neighbors, linear regression, logistic regression, random forest, gradient boosted machine (GBM), deep learning, a deep neural network, and/or any other suitable machine-learning technique that solves problems in the field of Natural Language Processing (NLP). Supervised, semi-supervised, and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

In an exemplary use case, a machine-learning model may be trained to classify a set of documents into one of a plurality of classes. The plurality of classes may also include an indeterminate or not-in-report class. In some aspects, a document in the indeterminate class may contain information that cannot be confidently classified into one of the classes, or the indeterminate class may contain multiple segments of text that can be individually classified into one of the classes that do not agree with each other. For a document in the not-in-report class, the result of the classification may result from a determination that the analyzed document does not contain any information regarding the plurality of classes. The machine-learning model may be trained on a training set of documents that are each already associated with a class of a plurality of classes, or a training set of documents of which a subset have already been associated with a class of a plurality of classes. The training may include the machine-learning model computing a training relevance metric for each document. Then, for each class, the machine-learning model may average the training relevance metric for all the documents in the training set that are associated with the same class. This may produce the average training relevance metric for each class of the plurality of classes. The machine-learning model may determine the class that has the highest average training relevance metric and classify the document as corresponding to such class.

In another exemplary use case, a machine-learning model may be trained to classify a set of medical reports, such as a set of radiology reports, into one of a plurality of classes. The plurality of classes may also include an indeterminate or not-in-report class, e.g., as described above. The machine-learning model may be trained on a training set of medical reports that are each already associated with a class of a plurality of classes, or a training set of medical reports of which a subset have already been associated with a class of a plurality of classes. The training may include the machine-learning model computing a training relevance metric for each medical report. Then, for each class, the machine-learning model may average the training relevance metric for all the medical reports in the training set that are associated with the same class. This produces the average training relevance metric for each class of the plurality of classes. The machine-learning model may then determine the class that has the highest average training relevance metric and classify the medical report as corresponding to such class.

In another exemplary use case, a machine-learning model may be trained to classify a set of breast imaging reports, such as a mammogram report, into one of a plurality of breast density classes. Such breast density classes may include a fatty class (Class A), a scattered fibroglandular density class (Class B), a heterogeneously dense class (Class C), and an extremely dense class (Class D). The breast density classes may also include an indeterminate or not-in-report class. As discussed above, a document in the indeterminate class may contain information that cannot be confidently classified into one of the classes, or the indeterminate class may contain multiple segments of text that can be individually classified into one of the classes that do not agree with each other. For example, a breast density report may be classified as indeterminate if it reports two different breast densities for the right and left breast, or if the wording used to describe the density cannot unambiguously be classified as one of the breast density classes. The result of an indeterminate classification may reflect a determination that the analyzed document does not contain any information regarding the classes. The training may include the machine-learning model computing a training relevance metric for each breast imaging report. Then, for each breast density class, the machine-learning model may average the training relevance metric for all of the breast imaging reports that are associated with the same breast density class, or a training set of breast imaging reports of which a subset have already been associated with a breast density class. This produces the average training relevance metric for each of the plurality of breast density classes. The machine-learning model may then determine the breast density class that has the highest average training relevance metric and classify the breast imaging report as corresponding to such class.

While several of the examples above involve medical reports, specifically radiology reports such as breast imaging reports, techniques according to this disclosure may be adapted to any suitable type of document from which text may be extracted. It should also be understood that the examples above are illustrative only. The techniques and technologies of this disclosure may be adapted to any suitable activity.

Presented below are various aspects of machine-learning techniques that may be adapted to automatically extract information from a document. As will be discussed in more detail below, machine-learning techniques adapted to extract textual information from a document and classify the document based on such extracted textual information may include one or more aspects according to this disclosure, e.g., a particular selection of training data, a particular training process for the machine-learning model, operation of a particular device suitable for use with the trained machine-learning model, operation of the machine-learning model in conjunction with particular data, modification of such particular data by the machine-learning model, etc., and/or other aspects that may be apparent to one of ordinary skill in the art based on this disclosure.

FIG. 1 depicts an exemplary environment 100 that may be utilized with techniques presented herein. One or more user device(s) 105, one or more external system(s) 110, and one or more server system(s) 115 may communicate across a network 101. As will be discussed in further detail below, one or more server system(s) 115 may communicate with one or more of the other components of the environment 100 across network 101. The one or more user device(s) 105 may be associated with a user, e.g., a user associated with one or more of generating, training, or tuning a machine-learning model for extracting information from a document, generating, obtaining, and/or analyzing document data. For example, the one or more user device(s) 105 may be associated with a doctor, a patient, a nurse, a medical specialist, or the like.

In some embodiments, the components of the environment 100 are associated with a common entity, e.g., a hospital, clinic, medical specialist, research center, document analysis center, or the like. In some embodiments, one or more of the components of the environment is associated with a different entity than another. The systems and devices of the environment 100 may communicate in any arrangement. For example, one or more user device(s) 105 may be associated with one or more patient-interfacing sites, and server system 115 may be associated with a research site responsible for receiving documents from the one or more patient-interfacing sites. As will be discussed herein, systems and/or devices of the environment 100 may communicate in order to one or more of generate, train, and/or use a machine-learning model to extract information from a document, among other activities.

The user device 105 may be configured to enable the user to access and/or interact with other systems in the environment 100. For example, the user device 105 may be a computer system such as, for example, a desktop computer, a mobile device, a tablet, etc. In some embodiments, the user device 105 may include one or more electronic application(s), e.g., a program, plugin, browser extension, etc., installed on a memory of the user device 105.

The user device 105 may include a display/user interface (UI) 105A, a processor 105B, a memory 105C, and/or a network interface 105D. The user device 105 may execute, by the processor 105B, an operating system (O/S) and at least one electronic application (each stored in memory 105C). The electronic application may be a desktop program, a browser program, a web client, or a mobile application program (which may also be a browser program in a mobile O/S), an applicant specific program, system control software, system monitoring software, software development tools, or the like. For example, environment 100 may extend information on a web client that may be accessed through a web browser. In some embodiments, the electronic application(s) may be associated with one or more of the other components in the environment 100. The application may manage the memory 105C, such as a database, to transmit streaming data to network 101. The display/UI 105A may be a touch screen or a display with other input systems (e.g., mouse, keyboard, etc.) so that the user(s) may interact with the application and/or the O/S. The network interface 105D may be a TCP/IP network interface for, e.g., Ethernet or wireless communications with the network 101. The processor 105B, while executing the application, may generate data and/or receive user inputs from the display/UI 105A and/or receive/transmit messages to the server system 115, and may further perform one or more operations prior to providing an output to the network 101.

The electronic application, executed by the processor 105B of the user device 105, may generate one or many points of data that can be applied via an overall system, such as for a document extraction platform. As an example, the user device 105 may be, e.g., a medical records system or a medical device that receives one or more medical reports, such as a breast imaging report.

External systems 110 may be, for example, one or more third party and/or auxiliary systems that integrate and/or communicate with the server system 115 in performing various document information extraction tasks. External systems 110 may be in communication with other device(s) or system(s) in the environment 100 over the one or more networks 101. For example, external systems 110 may communicate with the server system 115 via API (application programming interface) access over the one or more networks 101, and also communicate with the user device(s) 105 via web browser access over the one or more networks 101.

In various embodiments, the network 101 may be a wide area network ("WAN"), a local area network ("LAN"), a personal area network ("PAN"), or the like. In some embodiments, network 101 includes the Internet, and information and data provided between various systems occurs online. "Online" may refer to connecting to or accessing source data or information from a location remote from other devices or networks coupled to the Internet. Alternatively, "online" may refer to connecting or accessing a network (wired or wireless) via a mobile communications network or device. The Internet is a worldwide system of computer networks—a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

The server system 115 may include an electronic data system, e.g., an electronic medical data system, computer-readable memory such as a hard drive, flash drive, disk, etc. In some embodiments, the server system 115 includes and/or interacts with an application programming interface for exchanging data to other systems, e.g., one or more of the other components of the environment. The server system 115 may include and/or act as a repository or source for extracted document information data.

The server system 115 may include a database 115A and at least one server 115B. The server system 115 may be a computer, system of computers (e.g., rack server(s)), and/or or a cloud service computer system. The server system may store or have access to database 115A (e.g., hosted on a third party server or in memory 115E). The server(s) may include a display/UI 115C, a processor 115D, a memory 115E, and/or a network interface 115F. The display/UI 115C may be a touch screen or a display with other input systems (e.g., mouse, keyboard, etc.) for an operator of the server 115B to control the functions of the server 115B. The server system 115 may execute, by the processor 115D, an operating system (O/S) and at least one instance of a servlet program (each stored in memory 115E). When user device 105 sends a document to the server system, the received documents and/or document information may be stored in memory 115E or database 115A. The network interface 115F may be a TCP/IP network interface for, e.g., Ethernet or wireless communications with the network 101.

The processor 115D may include a trained classifier 120, which may include a preprocessing module 120A, a relevance metric computation module 120B, a similarity score module 120C, and/or a document classification module 120D. The trained classifier 120 may include instructions for automatically extracting information from a document. The preprocessing module 120A may include instructions for preprocessing a document. The relevance metric computation module 120B may include instructions for computing a relevance metric. The similarity score module 120C may include instructions for computing a similarity score for each of the plurality of classes, where the similarity score may indicate the similarity between language in a document and language indicative of a class of the plurality of classes. The document classification module 120D may include instructions for classifying a document. The preprocessing module 120A, the relevance metric computation module 120B, the similarity score module 120C, and/or the document classification module 120D may be contained within the trained classifier 120. Alternatively, some or all of such modules may be submodules of other modules within each other. For example, the preprocessing module 120A, the relevance metric computation module 120B, and/or the similarity score module 120C may be submodules of the document classification module 120D.

As discussed in further detail below, the server system 115 may generate, store, train, or use a machine-learning model, such as the trained classifier 120, configured to extract document information and/or classify a document based on the extracted information. The server system 115 may include a machine-learning model and/or instructions associated with the machine-learning model, e.g., instructions for generating a machine-learning model, training the machine-learning model, using the machine-learning model, etc. The server system 115 may include instructions for retrieving document information data, e.g., based on the output of the machine-learning model, and/or operating the display 115C to output document information data, e.g., as adjusted based on the machine-learning model. The server system 115 may include training data, e.g., a set of documents, a set of medical reports, and/or a set of breast density reports.

In some embodiments, a system or device other than the server system 115 is used to generate and/or train the machine-learning model. For example, such a system may include instructions for generating the machine-learning model, the training data and ground truth, and/or instructions for training the machine-learning model. A resulting trained machine-learning model may then be provided to the server system 115.

In some embodiments, the trained classifier 120 may be trained in environment 100 with user device(s) 105, external system(s) 110, and server system 115 connected via network 101. The trained classifier 120 may then be isolated and extracted from environment 100 into a different environment, such as a different clinical study or different clinical information system, in order to perform the classification of documents contained in a database that was not present during the training of the trained classifier 120.

Generally, a machine-learning model includes a set of variables, e.g., nodes, neurons, filters, etc., that are tuned, e.g., weighted or biased, to different values via the application of training data. In supervised learning, e.g., where a ground truth is known for the training data provided, training may proceed by feeding a sample of training data into a model with variables set at initialized values, e.g., at random, based on Gaussian noise, a pre-trained model, or the like. The output may be compared with the ground truth to determine an error, which may then be back-propagated through the model to adjust the values of the variable.

Training may be conducted in any suitable manner, e.g., in batches, and may include any suitable training methodology, e.g., stochastic or non-stochastic gradient descent, gradient boosting, random forest, etc. In some embodiments, a portion of the training data may be withheld during training and/or used to validate the trained machine-learning model, e.g., compare the output of the trained model with the ground truth for that portion of the training data to evaluate an accuracy of the trained model. The training of the machine-learning model may be configured to cause the machine-learning model to learn associations between the document information data and the associated classification data, such that the trained machine-learning model is configured to determine an output classification in response to the input document information data based on the learned associations.

In various embodiments, the variables of a machine-learning model may be interrelated in any suitable arrangement in order to generate the output. For example, in some embodiments, the machine-learning model may include signal processing architecture that is configured to identify, isolate, and/or extract features, patterns, and/or structure in a text. For example, the machine-learning model may include one or more convolutional neural network ("CNN") configured to identify features in the document information data, and may include further architecture, e.g., a connected layer, neural network, etc., configured to determine a relationship between the identified features in order to determine a location in the document information data. Furthermore, in other embodiments, processor 105B, processor 115D, and/or preprocessing module 120A may include known optical character recognition (OCR) techniques that transform an incoming document image, such as a scanned or faxed document, into a text that is suitable as input for document classification module 120B.

For example, in some embodiments, the machine-learning model of the server system 115 may include a Recurrent Neural Network ("RNN"). Generally, RNNs are a class of feed-forward neural networks that may be well adapted to processing a sequence of inputs. In some embodiments, the machine-learning model may include a Long Short Term Memory ("LSTM") model and/or Sequence to Sequence ("Seq2Seq") model. An LSTM model may be configured to generate an output from a sample that takes at least some previous samples and/or outputs into account. A Seq2Seq model may be configured to, for example, receive a sequence of letters or words as input, and generate a sequence of locations, e.g., a path of relevant text passages in the report as output.

Although depicted as separate components in FIG. 1, a component or portion of a component in the environment 100 may, in some embodiments, be integrated with or incorporated into one or more other components. For example, a portion of the display 115C may be integrated into the user device 105 or the like. In some embodiments, operations or aspects of one or more of the components discussed above may be distributed amongst one or more other components. Any suitable arrangement and/or integration of the various systems and devices of the environment 100 may be used.

Further aspects of the machine-learning model and/or how it may be utilized to automatically extract document information are discussed in further detail in the methods below. In the following methods, various acts may be described as performed or executed by a component from FIG. 1, such as the server system 115, the user device 105, or components thereof. However, in various embodiments, various components of the environment 100 discussed above may execute instructions or perform acts including the acts discussed below. An act performed by a device may be considered to be performed by a processor, actuator, or the like associated with that device. Further, in various embodiments, various steps may be added, omitted, and/or rearranged in any suitable manner.

Training a Machine-Learning Model to Classify a Document

Figure 2:
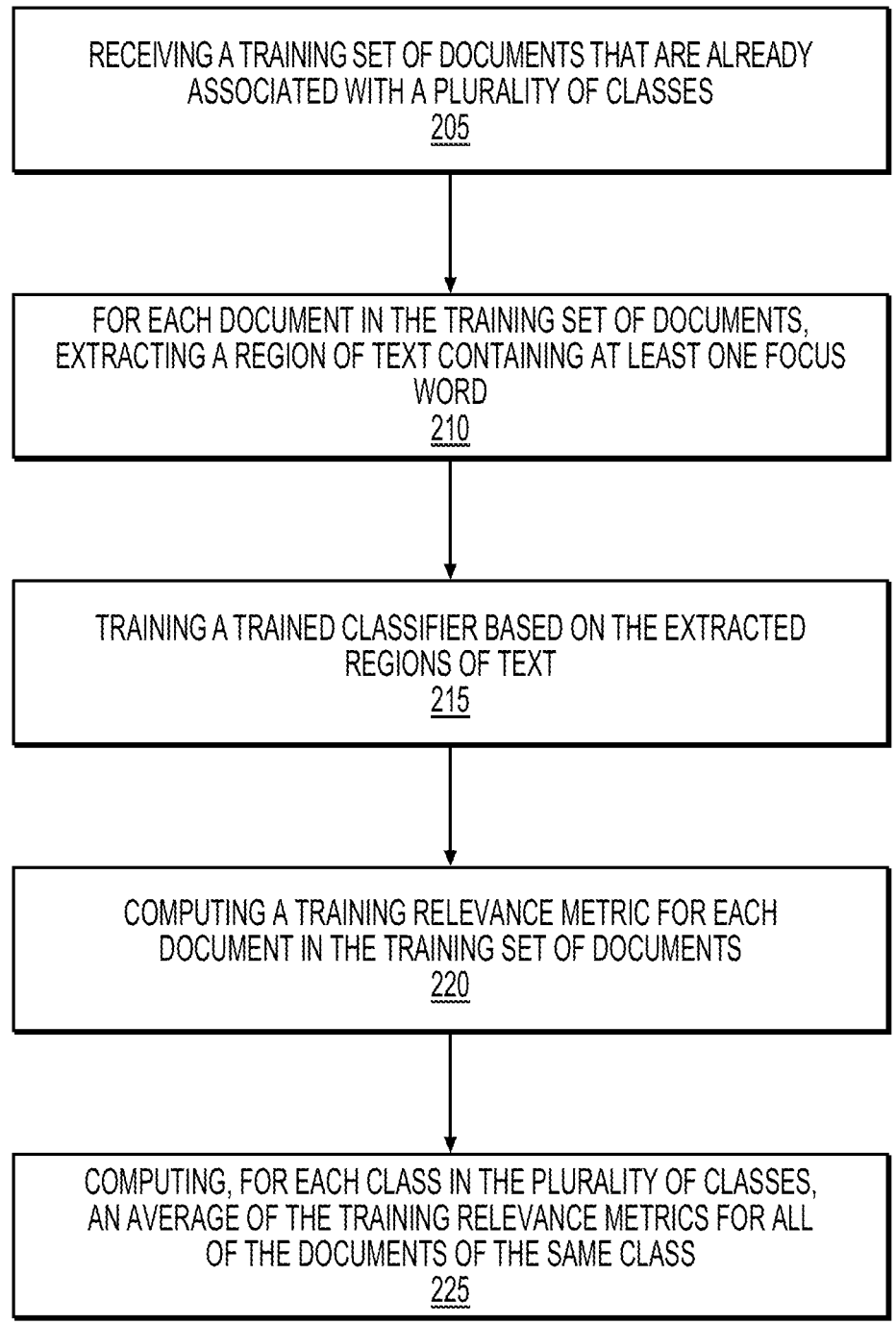
FIG. 2 depicts a flowchart of an exemplary method of training a machine-learning model to classify a document into one of a plurality of classes, according to one or more embodiments.

FIG. 2 illustrates an exemplary process for training a machine-learning model, such as a trained classifier (e.g., trained classifier 120), to classify a document into one of a plurality of classes, such as in the various examples discussed above. The assumption underlying the training and classification methods described herein is that documents including language that can be classified into one of a plurality of classes may be relevant to different terms to different extents. Based on this property, the trained classifier can approximate a signature for each class, and then assess how relevant a given document is to the signature for each class.

At step 205 of the training process, the method may include receiving a training dataset, e.g., a training set of documents that are already associated with a plurality of classes. In some aspects, each document in the training set may contain digital text (e.g., typed text, etc.), paper text (e.g., printed text, handwritten text, etc.), or a combination thereof. In some aspects, the training set of documents associated with a plurality of classes may be a subset of a larger training set of documents received, some of which may not be associated with a plurality of classes. The training set of documents may be, for example, free text documents, e.g., free text medical reports and/or free text breast imaging reports, such as mammogram reports. If the training set of documents includes breast imaging reports, for example, the plurality of classes with which the documents are associated may include at least one of a fatty class (Class A), a scattered fibroglandular density class (Class B), a heterogeneously dense class (Class C), an extremely dense class (Class D), and an indeterminate class.

Although medical reports, for example, breast imaging reports, are discussed herein, any type of medical report (e.g., radiology reports, such as brain imaging reports, orthopedic imaging reports, etc., pathology reports associated with tissue samples, and medical reports not associated with an imaging read, e.g., clinician notes in patient charts) may be used as the set of documents, depending on the different applications of the methods described herein. Further, non-medical documents, such as application submissions, driving records, or any suitable type of documents containing unstructured or structured textual information may be used in conjunction with a variety of relevant non-medical classifications. The set of documents may be associated with a plurality of classes relevant to the type of documents used.

A server system (e.g., server system 115) may receive the set of documents, and the server system (e.g., server system 115) may store the set of documents in a database (e.g., database 115A) or in a memory (e.g., memory 115E). Additionally, for example, a user may upload the set of documents to a user device (e.g., user device 105), or a display (e.g., display 105A) may prompt the user to directly enter the contents of the set of documents. The user device (e.g., user device 105) may or may not store the set of documents in the memory (e.g., memory 105C). The user device (e.g., user device 105) may then send the set of documents to the server system (e.g., server system 115) via a network (e.g., network 101).

At step 210, the method may include, for each document in the training set of documents, extracting a region of text containing at least one focus word. In situations where a document is fully or partially embodied as paper text, an OCR process may be implemented to electronically convert the paper text content within the document to machine-encoded text (i.e., digital text). The method may further include, for each document in the training set of documents, using a focus region search. The focus region search may identify targeted regions of the document, e.g., regions containing words relevant to the plurality of classes (e.g., words relevant to breast density in the mammogram imaging example). The relevant words may be referred to herein as "focus words." Focus words may include a single word or a phrase. In some aspects, step 210 may include extracting a region of text containing at least one focus word, where a relevance metric computation module (e.g., relevance metric computation module 120B) may perform the extracting.

The list of relevant focus words may be predetermined and may include a set of words identified by an entity familiar with the type of document being analyzed. The selection of focus words may allow the method to be tailored to the type of documents and data within the documents being analyzed. For example, a list of relevant focus words for a medical report (e.g., radiology report) may have been generated by a clinician in a relevant specialty (e.g., a radiologist or other clinician trained in treating and/or diagnosing a particular disease, for example, a clinician trained in diagnosing and/or treating breast cancer in the example of mammography reports). For the example in which the set of documents consists of mammography reports, and the classes include classes A (fatty), B (scattered fibroglandular density), C (heterogeneously dense), and D (extremely dense), as described above, the focus words may be relevant to breast density type. In this scenario, the at least one focus word may include, for example, dense, density, densities, heterogeneous, heterogeneously, scattered, fibroglandular, fat, fatty, extreme, extremely, moderate, mildly, largely, entirely, fatty replaced, average, and/or scattered areas of fibroglandular density. Some focus words may directly carry information that indicates an association with one of the classes, while some focus words may carry information that indicates that the region of text around the focus word may include relevant information, even if such focus words are not themselves specific to a particular class.

In the previous examples, fat, fatty, and entirely point to class A, scattered, fibroglandular, and scattered areas of fibroglandular density point to class B, heterogeneous and heterogeneously point to class C, and extreme and extremely point to class D. However, dense, density, densities, moderate, mildly, largely, fatty replaced, and average may indicate the presence of a text passage with information on breast density, even though these words themselves don't point to a specific class. Independent of the initial indication of a focus word, subsequent machine learning may be applied to classify a text region identified by the presence of focus words. For example, negated statements like "the breasts do not appear to be entirely fatty" and unrelated statements like "the image quality is extremely low" may be identified as containing focus words, while the final classification result is not indicated by the focus words. If other types of documents are being analyzed to classify other types of data contained within those documents into one of a plurality of classes, then focus words specific to that data and the relevant classes may be selected. This may allow the systems and methods to be tailored for classifying a variety of different documents and for analyzing a variety of different data contained within those documents. In some aspects, a passage or statement may not be "in focus" (i.e., the text passage is not relevant for classification purposes) despite containing one or more focus words. More particularly, machine learning techniques may be applied to identify a context of a passage (e.g., by examining the relationship between the focus words and the surrounding words and/or phrases in a passage) and to ultimately determine that the passage is contextually irrelevant to classification and should therefore not be considered as being in focus for a subsequent training or scoring task.

The use of focus words may shrink the variation of the training set, allowing for more emphasis to be put on focus regions deemed as important and the relevant words that appear in those focus regions. Doing so may allow for a smaller feature set (or dictionary in language speak), which may provide improved training on a smaller number of training examples.

Using a focus region may be beneficial in documents in which relevant information appears in a few isolated places in each document. Use of a focus region in conjunction with the focus words may allow the classifier to consider and focus on regions of text surrounding the focus words that are relevant to the information contained in the document that can help to classify the document, which may eliminate irrelevant text and strengthen the signal from the data.

At step 215, the method may include training a trained classifier (e.g., trained classifier 120) based on the extracted region of text containing at least one focus word. For example, the classifier extracts regions of text around the focus words in the training data and may train on those focus regions.

At step 220, the method may include computing the training relevance metric for each document in the training set of documents, where the relevance metric computation module (e.g., relevance metric computation module 120B) may perform the computing. The training relevance metric may correspond to each term that appears in a set of documents. Such terms may be provided by subject matter experts in the relevant field. In some aspects, the terms may be determined by unsupervised or supervised clustering of training documents or regions in training documents, which have been annotated by subject matter experts to contain relevant information. The terms may be characterized by a training relevance metric computed from frequency statistics, which capture how often a term may occur in text passages indicative of a class, how often a term may occur in text passages that are not indicative of a class, and what fraction of an input text carries relevant information. A training reference metric may be high if a term occurs frequently in text passages indicative of a class, and rarely in text passages in input documents that are not indicative of a class. For example, the training relevance metric may be computed as a training term frequency-inverse document frequency (tf-idf) vector, a word2vec algorithm, one hot encoding, or other vector text representations for text data, that corresponds to each focus region for each report. The relevance metric, e.g., tf-idf vector, allows the system to measure how relevant a document is to a certain term. A document that is highly relevant to a given term may be one in which the term appears frequently relative to the number of documents that contain the term. Thus, to capture a document's relevance overall, the method may compute a vector of relevance metric scores, e.g., tf-idf scores, corresponding to each term that appears in the set of documents.

As discussed above, the underlying assumption is that a document that includes relevant information may be relevant to different terms to different extents. For example, a mammogram report describing different breast density types may be relevant to different terms to different extents. Based on this property, the system may approximate a training relevance metric signature, e.g., tf-idf signature, for each class. A tf-idf signature may be a specific tf-idf vector, where the tf-idf signature may be computed by averaging the tf-idf vectors for all of the training documents of a certain class. In the case of breast density, a training relevance metric signature, e.g., tf-idf signature, may be approximated for each breast density class. Given a training set of mammogram reports with associated classifications, the system may compute the relevance metric vector, e.g., tf-idf vector, for each report. Or, more generally, given a training set of another type of documents, the system may compute the training relevance metric vector, e.g., tf-idf vector, for each document in the training set.

At step 225, the method may include computing, for each class in the plurality of classes, an average of the training relevance metrics for all documents in the training set of documents of the same class. A relevance metric computation module (e.g., relevance metric computation module 120B) may perform the computing. The averaging of the training relevance metrics for all documents may be computed by taking all of the words in the regions of interest (those within some range of the focus words), where the regions of interest are accumulated for training examples in the same class, and then computing the result vector with regards to the relevance metric. This process may be repeated for all of the documents in the training set of documents. At step 225, the classifier may average all of the training relevance metrics for all of the documents of the same class, resulting in a single average training relevance metric vector for each class in the plurality of classes. The single average training relevance metric for each class in the plurality of classes may be produced, or displayed, on a server display (e.g., display 115C) and/or a user device display (e.g., display 105A), or it may be stored in a server system memory (e.g., memory 115E), a server system database (e.g., database 115A), and/or a user device memory (e.g., memory 105C).

If the training relevance metric is a tf-idf vector, for example, the relevance metric computation module (e.g., relevance metric computation module 120B) may compute the average tf-idf vector for each class of the plurality of classes. This process may be repeated for all of the documents in the training set of documents. All of the tf-idf vectors for the same class of all the documents in the set of documents may then be added and divided by the number of documents in the set of documents, resulting in the average tf-idf vector.

Another example of computing the average of the training relevance metric, such as a tf-idf vector, may be selecting a certain number of the highest averages of the training relevance metric of documents in the training set of documents that belong to the same class. For example, the five highest training relevance metric averages of the documents of the same class may be selected, added, and divided by five to determine the training relevance metric for the class. In this example, the n highest training relevance metric averages of the documents of the same class may be selected, added, and divided by n to determine the training relevance metric for the class, wherein n is a number greater than zero and less than the number of documents in the training set of documents that belong to the same class. This process may be repeated for all of the classes, resulting in an average training relevance metric for each class.

Figure 3:
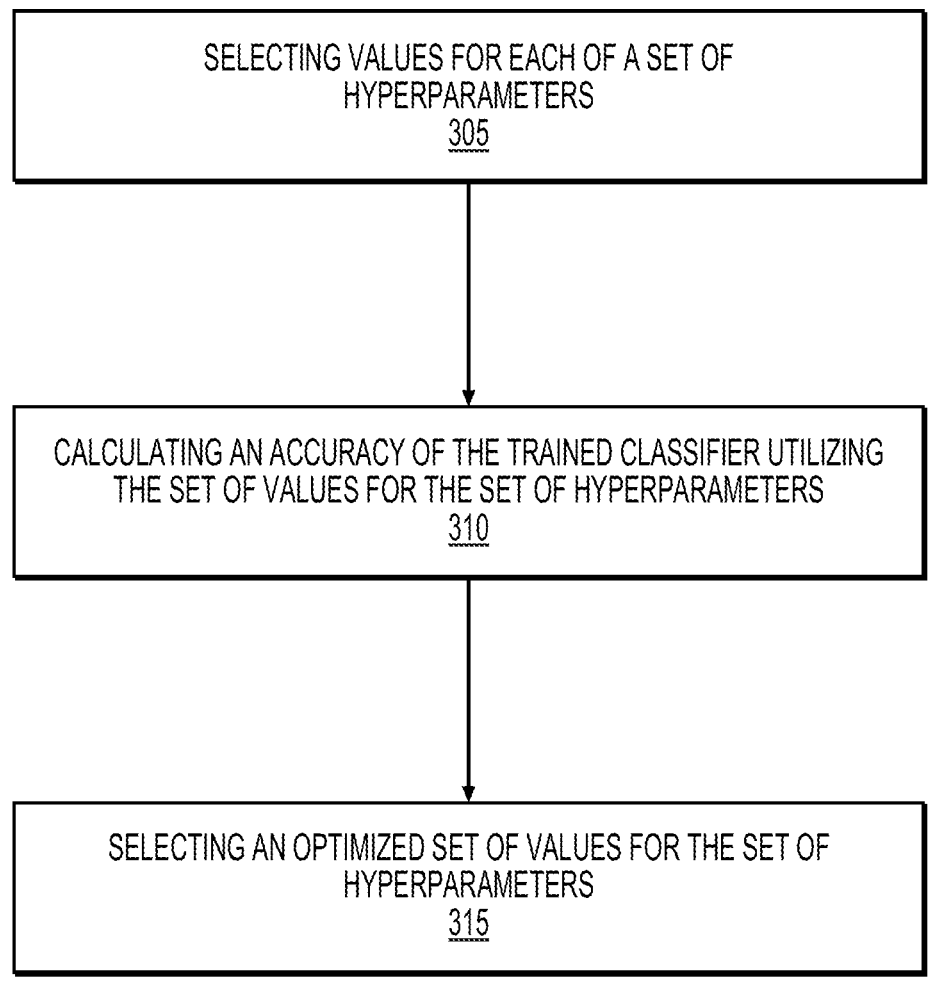
FIG. 3 depicts a flowchart of an exemplary method of training a machine-learning model to classify a document by optimizing a set of hyperparameters using an iterative grid search algorithm, which is based on a training set of documents, according to one or more embodiments.

FIG. 3 illustrates an exemplary process for training a machine-learning model, such as a trained classifier (e.g., trained classifier 120), to classify a document by optimizing a set of hyperparameters using an iterative grid search algorithm based on a training set of documents, e.g., by utilizing a trained machine-learning model such as a machine-learning model trained according to one or more embodiments discussed above. In some aspects, the method of FIG. 3 may be performed in combination with the methods of FIG. 2 and/or FIG. 4, e.g., simultaneously or following the methods of FIG. 2 and/or FIG. 4.

At step 305, the method may include selecting values for each of a set of hyperparameters, where an optimizer (e.g., optimizer 125) may perform the selecting. The trained classifier (e.g., trained classifier 120) may have a set of four hyperparameters that may affect its accuracy. Such hyperparameters may include at least one of (i) a size of the sliding window region, which is the number of words in a document that are compared to a training relevance metric to determine the correct classification, (ii) a size of a focus region around a focus word, where the size of the focus region is the number of words around the focus word incorporated into training, (iii) a number of highest window similarity scores in a subset on which to base the overall similarity scores for the document, and (iv) a not-in-report, or indeterminate, threshold. The value of the hyperparameters may be kept constant during training, which includes optimization, as well as application or testing.

The size of each sliding window region and the size of the focus region may be expressed as the number of characters and/or the number of words. The number of characters and/or the number of words can be at least 0, 1, 2, 3, 4, 5, 6, 7, 8, 9, 10 or more. The number of characters and/or the number of words can be at most 10, 9, 8, 7, 6, 5, 4, 3, 2 or less. The sliding window moves across a document, scanning the document, and the size of the sliding window region is the number of words that will be included in each window region as this scanning takes place. The size of a focus region around a focus word represents the total number of words around the focus words that are considered during training, with the focus word being the middle word. If the focus word is a phrase (e.g., "scattered areas of fibroglandular density"), then the entire phrase may be considered the middle 'word.' In that case, if the size of the focus region were three, and the focus word was "scattered areas of fibroglandular density," then one word on either side of the phrase "scattered areas of fibroglandular density" would be extracted.

The number of highest similarity scores in the subset will be discussed further below, and may be all of the similarity scores in a document, or it may be a smaller number of similarity scores than all of the similarity scores in the document. In some aspects, the number of highest similarity scores in the subset may be the single highest similarity score in the document.

The threshold may be a minimum threshold similarity score that the highest similarity score meets and/or surpasses in order to avoid an indeterminate or "not-in-report" result. For example, if the highest similarity score does not meet and/or surpass the threshold, it may mean that even though there may be some similarity of the document to a given class, there is not enough similarity for the system to conclusively determine that the similarity relates to the particular class. In some aspects, not meeting the threshold may indicate that the relevant information may not be contained within the document.

To select the values for each of the hyperparameters, the optimizer (e.g., optimizer 125) may use an iterative grid search. The iterative grid search may be performed by picking a list of values for each hyperparameter, and then trying out all possible combinations of such values within reason. The set of hyperparameters may be treated as coordinates in a multi-dimensional space, with the number of dimensions equaling the number of hyperparameters used. The coordinates may be bounded by reasonable limits. For example, reasonable limits of the window size may be from one to the length of the shortest document. Additionally, for example, the complete bounds of the coordinates may include 0.0 to 0.1. Furthermore, for example, when the four hyperparameters listed above are used, the optimizer (e.g., optimizer 125) selects four numbers—one for each hyperparameter—at random, and within reasonable limits.

At step 310, the method may include calculating an accuracy of the trained classifier (e.g., trained classifier 120) utilizing the set of values for the set of hyperparameters. For example, on each iteration, a k fold cross-validation may be run, and then the accuracy may be evaluated as the average of k testing subsets. The optimizer (e.g., optimizer 125) may perform the calculating. As discussed above, the set of hyperparameters may be treated as coordinates in a multi-dimensional, in this example, four-dimensional, space. At regular intervals in the space, the optimizer (e.g., optimizer 125) may calculate the accuracy of the classifier using the selected values for each hyperparameter. The optimizer (e.g., optimizer 125) may check every nth coordinate, e.g., every fifth or tenth coordinate. The optimizer (e.g., optimizer 125) may check points along graph lines rather than between graph lines. The trained classifier (e.g., trained classifier 120) may utilize the selected set of values for the set of hyperparameters when analyzing a set of documents. The optimizer (e.g., optimizer 125) may compare the results of such analysis with the expected results, and then calculate the accuracy based on the results of such comparison.

The accuracy of the trained classifier may be defined as the number of test cases that the classifier correctly classified. For example, a k-fold cross validation may be used to train and test the classifier. The k-fold cross validation may include randomly dividing a labeled dataset into k segments, where k may be an integer. The step of randomly dividing may include performing this random division separately for the training documents of each class, such that the created folds have approximately the same number of training documents for each class. For example, a labeled dataset may be divided into ten segments, where k equals ten. Then, the classifier may be trained using k−1 of the segments, and then may test itself on the remaining k segment. This process may be repeated k times, using a different segment for testing each time, and the accuracy from each run may be averaged. For example, expanding on the previous example with k=10, the classifier may be trained using nine of the 10 segments and then the classifier may be tested on the remaining one segment. This run may be repeated ten times, using a different segment for testing each time. The accuracy for each run may be averaged, in order to calculate the accuracy for each of the ten segments. An advantage to this method is that each labeled data point may be used for testing exactly once, so the calculated accuracy may not be biased by the specific subset of the labeled data points that are used for testing.

At step 315, the method may include selecting an optimized set of values for the set of hyperparameters, where the optimizer (e.g., optimizer 125) may perform the selecting. Such a process may be referred to as a sparse grid search. The optimizer (e.g., optimizer 125) may zoom in on a region of hyperparameter values that yields the best accuracy and continue to select values that yield a more improved accuracy. The optimizer (e.g., optimizer 125) may select the single point that gave the best accuracy, and then zooms in on the region around that point, and runs the search again at a higher resolution. The region of selected values may be bounded by reasonable value limits. The method may repeat step 310 for each set of selected hyperparameter values until the optimal set of values have been selected at step 315. Such selected optimal values may be deemed the optimal hyperparameter values.

The Machine-Learning Model Automatically Classifying a Document

Figure 4:
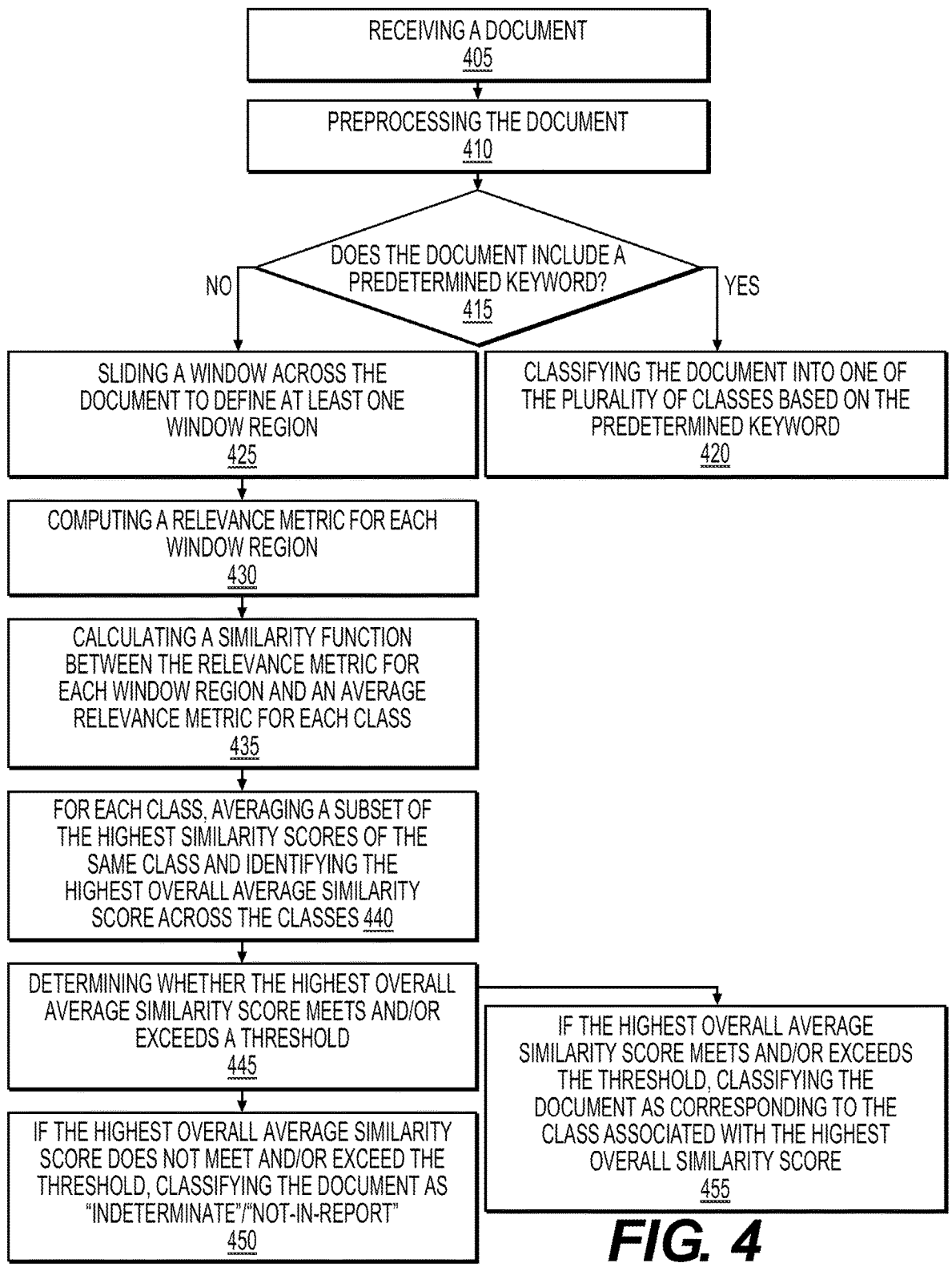
FIG. 4 depicts a flowchart of an exemplary method for automatically classifying a document, according to one or more embodiments.

FIG. 4 illustrates an exemplary process for automatically extracting information from a document to classify the document, e.g., by utilizing a trained machine-learning model, such as a machine-learning model trained according to one or more embodiments discussed above.

At step 405, the method may include receiving a document, where the document contains textual information. In some aspects, the document may contain digital text (e.g., typed text, etc.), paper text (e.g., printed text, handwritten text, etc.), or a combination thereof. The document may be a free text document, for example, a medical report, such as a radiology report, and, more particularly in some aspects, a breast imaging report, such as a mammogram report. The document may be received by a user device (e.g., user device 105) and sent via a network (e.g., network 101) to a server system (e.g., server system 115), which then receives the document. The document may also be received directly by the server system (e.g., server system 115). The server system may store the document in a database (e.g., database 115A) or in a memory (e.g., memory 115E).

At step 410, the method may include preprocessing the document. The preprocessing may be performed by a preprocessing module (e.g., preprocessing module 120A). The preprocessing may include at least one of: formatting the document, removing at least one stopword from the document, and/or stemming at least one word in the document.

In situations where a document is fully or partially embodied as paper text, an OCR process may be implemented to electronically convert the paper text content within the document to machine-encoded text (i.e., digital text), which may allow stopword removal and/or stemming to more easily be performed.

The removing at least one stopword from the document during preprocessing step 410 may include removing common words from the document that are not likely to encode relevant information. For example, the at least one stopword may include at least one of: it, what, is, are, the, a, an, and/or those. Such a process may reduce the dimensionality of the document information, simplifying the text and making it easier to extract relevant document information.

The stemming at least one word in the document during preprocessing step 410 may include removing the inflection from various forms of the same root word. For example, if "running" and "runs" were in the document, both words may map to "run." Such a process may reduce the dimensionality of the document information, simplifying the text and making it easier to extract useful document information.

In some exemplary methods classifying methods, an optional step 415 may be performed. Step 415 may include determining whether a document includes at least one predetermined keyword (e.g., individual key words or key phrases). For example, if a document is a breast imaging report the at least one predetermined keyword may include at least one of: "the breasts are almost entirely fat" (Class A), "the rest of the breasts are mildly dense" (Class B), "there are scattered densities throughout the breast" (Class B), "the breast tissue is dense" (Class C), "the breasts are heterogeneously dense, which may obscure small masses" (Class C), and/or "the right breast is very dense" (Class D). Predetermined keywords may be stored in the trained classifier 120 together with coefficients, weights, and hyperparameters that comprise a training result.

If the document is determined to include at least one predetermined keyword, then optional step 420 may be performed. In optional step 420, the document may be classified into one of the plurality of classes based on the predetermined keyword. A keyword may be so directly correlated to a class of the plurality of classes that if the classifier finds the keyword in the document, it may rely on the presence of the keyword in the document to classify the document and may bypass the rest of method steps 425 through 455. For example, if the document is a breast imaging report and the report includes the predetermined keyword "fatty class," or "Class A," then the document may be automatically classified as a fatty class (Class A). As a result, by directly classifying the document using the keyword, the rest of the method steps may be omitted. For example, steps 425 through 455 of the method are not performed if the document includes a predetermined keyword, since the keyword can instead be used to classify the document.

The list of relevant keywords may be predetermined and may include a set of words identified by an entity familiar with the type of document being analyzed. The term "keyword," as used herein, may refer to a single word or a phrase. Different keywords may be associated with different classes of the plurality of classes, so that the trained classifier (e.g., trained classifier 120) may identify the presence of a keyword and then classify the document as associated with the class with which the keyword is associated. The selection of keywords may allow the method to be tailored to the type of documents and data within the documents being analyzed and classified. For example, a list of relevant keywords for a medical report (e.g., radiology report) may have been generated by a clinician in a relevant specialty (e.g., a radiologist or other clinician trained in treating and/or diagnosing a particular disease, for example, a clinician trained in diagnosing and/or treating breast cancer in the example of mammography reports). If other types of documents are being analyzed to classify other types of data contained within those documents into one of a plurality of classes, then keywords specific to that data and the relevant classes may be selected. This may allow the systems and methods to be tailored for classifying a variety of different documents and for analyzing a variety of different data contained within those documents.

If the document does not contain a predetermined keyword, or if optional step 415 is not performed, the method may proceed to step 425, where the method may include applying a sliding window search to slide a window across the document to define at least one window region, where the trained classifier (e.g., trained classifier 120) may perform the sliding window search. The trained classifier (e.g., trained classifier 120) may include a set of hyperparameters, as described above, which may include the size of each sliding window region. Accordingly, optimization of the hyperparameter may be used to define, among other things, the size of each sliding window region.

At step 430, the method may include computing a relevance metric for each window region, where the relevance metric computation module (e.g., relevance metric computation module 120B) may perform the computing. If there is more than one window region, the relevance metric may be computed for each window region. For example, the relevance metric may be computed as a tf-idf vector that corresponds to each window region.

At step 435, the method may include calculating a similarity function or distance function between the relevance metric for each window region and an average relevance metric for each class, where the similarity score module (e.g., similarity score module 120C) may perform the calculating. The calculated similarity function for each class may be assigned as the similarity score for each class's window region. For example, the relevance metric for each window may include a tf-idf vector, and the average relevance metric may be an average tf-idf vector for each class. As a result, a similarity function or distance function, such as a cosine similarity, city block distance, Cartesian distance, and/or Mahalanobis distance, may be calculated between the tf-idf vector for each window and the average tf-idf vector for each class. This means that each window region has a similarity score calculated for each class.

At step 440, the method may include computing an overall similarity score for the document. The overall similarity score for the document may be based on a subset of one or more highest similarity scores computed for each of the plurality of classes for each of the plurality of window regions. For example, the similarity score module (e.g., similarity score module 120C) may average a certain number, e.g., a subset, of the highest window similarity scores for the document for each class. The number of highest window similarity scores for each class to be averaged in a given document may be one or may be more than one. As discussed above, a hyperparameter may include the number of window similarity scores on which to base the overall similarity scores for a document. Optimization of the hyperparameter value may be used to determine the number of window similarity scores to average for each class, and this hyperparameter may have been optimized, e.g., during training. The hyperparameter may indicate a subset that equals or is less than the number of window regions in the document is to be averaged for each class. By way of further example, the hyperparameter may indicate that one similarity score, e.g., the highest similarity score for each class, can be in the subset. By way of other examples, two, three, four, five, six, seven, eight, nine, ten, or more of the highest similarity scores for each class may be in the subset, in accordance with the hyperparameter value identified by the optimizer (e.g., optimizer 125).

Trained classifier 120 (e.g., document classification module 120D) may identify the highest average similarity score across all of the classes as the highest overall average similarity score for the document. For example, the document classification module (e.g., document classification module 120D) may compare all of the highest averages of similarity scores for all of the classes to determine which class has the highest average similarity score, and the highest average similarity score may be assigned to the document as the highest overall average similarity score.

At step 445, the method may include determining whether the highest overall average similarity score meets and/or exceeds a threshold, where the document classification module (e.g., document classification module 120D) may perform the determining. As discussed above, a hyperparameter may include a not-in-report, and/or indeterminate, threshold. The hyperparameter value may be optimized and used to indicate the threshold value, where not meeting or exceeding the threshold value results in an indeterminate classification. For example, if the highest overall average similarity score does not meet or exceed the threshold value, then at step 450, the document may be classified as corresponding to an indeterminate class. The indeterminate classification may also result in a notification on one or both of the user display (e.g., display 105) or server display (e.g., display 115C). In some aspects, not meeting the threshold may indicate that the document lacks relevant information for classifying the document.

In some aspects, the threshold may include a difference value between the highest overall average and the second highest overall average similarity scores. If the difference does not meet or exceed the threshold, then the classifier may proceed to step for 450, where the document may be classified as corresponding to an indeterminate class. In other words, if the two highest overall average similarity scores are not different enough from each other, then the document may be classified as corresponding to an indeterminate class.

Since the classifications, such as breast density classifications, may fall along a spectrum, with some classes being more similar to each other than other classes, thresholds may help in determining if the document fits into one of two neighboring classifications. For example, descriptions of the Class A and Class B breast density may be very similar. If the highest overall average and the second highest overall average do not pass the threshold but belong to neighboring classes (e.g., Class A and Class B, as opposed to dissimilar classes at different ends of the spectrum, such as Class A and Class D), then the document may be classified as belonging to the class of the highest overall average. However, the document may be classified as corresponding to an indeterminate class if the highest overall average and the second highest overall average do not pass the threshold and do not belong to classes that neighbor each other, which may indicate, e.g., that relevant information is not being included, and random noise, namely words or successions of words similar to those identifying a class while not being indicative of a class, is being amplified. Additionally, the document may also be classified as corresponding to an indeterminate class if different window regions in the document have high similarities to different classes, each of which would, when seen alone, result in a classification as one of the different classes.

If the overall similarity score does meet or exceed the threshold, then at step 455, the method may include classifying the document as corresponding to the class with which the highest overall similarity score is associated with, where the document classification module (e.g., document classification module 120D) may perform the classifying.

The classifying may or may not include displaying the classification on a server display (e.g., display 115C) and/or a user device display (e.g., display 105A), or the classification may be stored in a server system memory (e.g., memory 115E), a server system database (e.g., database 115A), and/or a user device memory (e.g., memory 105C). The classifying may or may not further include a display of the document with sliding window regions and sliding window regions highlighted. The text highlighting style, such as bold text, italic text, and/or different text and background colors, may, in some aspects, be automatically chosen based on the classification result for each sliding window region.

In some aspects, such a classification may assist in predicting current conditions or future actions. For example, if the document is a medical report, the classification may be an indicator of a medical condition and/or treatment steps to be taken. By way of another example, the document may be a breast imaging report, where the classification may be a breast density classification. The breast density classification may be an indicator of a possible medical condition of a subject with which the report is affiliated with, such as indicating a possible medical condition of breast cancer and/or future actions, such as treatment steps, to be taken.

It is to be understood that the training method of FIG. 2, the hyperparameter optimization of FIG. 3, or the classifying method of FIG. 4 may be performed in any suitable order. For example, the method of FIG. 2 may be performed prior to the method of FIG. 3, which may be performed prior to FIG. 4, or may be performed in another order. Or, the methods of FIGS. 2, 3, and 4 may be performed at the same time as one another. For example, one or more of training, optimizing, or classifying may be performed synchronously with each other. In some aspects, whether performed one after another or synchronously, the methods of one or more of FIGS. 2, 3, and 4 may be performed repeatedly.

Training a Machine-Learning Model to Classify a Breast Imaging Report

Figure 5:
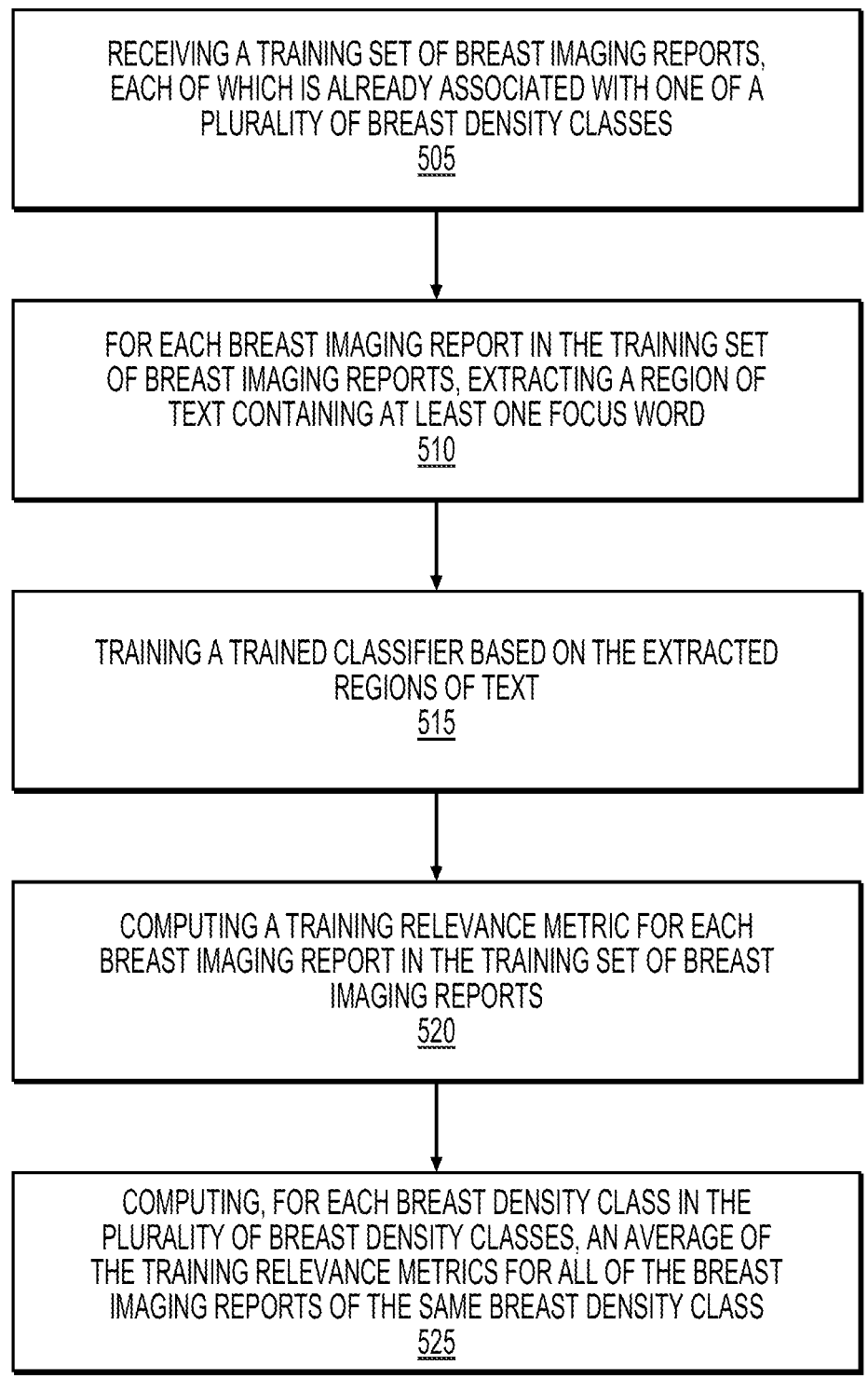
FIG. 5 depicts a flowchart of an exemplary method of training a machine-learning model to classify a breast imaging report into one of a plurality of breast density classes, according to one or more embodiments.

FIG. 5 illustrates an exemplary process for training a machine-learning model, such as a trained classifier (e.g., trained classifier 120), to classify a breast imaging report into one of a plurality of breast density classes, such as in the various examples discussed above.

At step 505, the method may include receiving a training dataset, e.g., a training set of breast imaging reports that are already associated with a plurality of breast density classes. In some aspects, each of the breast imaging reports in the training set may contain digital text (e.g., typed text, etc.), paper text (e.g., printed text, handwritten text, etc.), or a combination thereof. In some aspects, the training set of breast imaging reports associated with a plurality of breast density classes may be a subset of a larger received training set of breast imaging reports, some of which may not be associated with a plurality of breast density classes. The training set of breast imaging reports may be, for example, free text documents and/or free text mammogram reports. Additionally, for example, the plurality of breast density classes may include at least one of a fatty class (Class A), a scattered fibroglandular density class (Class B), a heterogeneously dense class (Class C), an extremely dense class (Class D), and an indeterminate class.

A server system (e.g., server system 115) may receive the set of breast imaging reports, and the server system (e.g., server system 115) may store the set of breast imaging reports in a database (e.g., database 115A) or in a memory (e.g., memory 115E). Additionally, for example, a user may upload the set of breast imaging reports to a user device (e.g., user device 105), or a display (e.g., display 105A) may prompt the user to directly enter the contents of the set of breast imaging reports. The user device (e.g., user device 105) may or may not store the set of breast imaging reports in the memory (e.g., memory 105C). The user device (e.g., user device 105) may then send the set of breast imaging reports to the server system (e.g., server system 115) via a network (e.g., network 101).

At step 510, the method may include, for each breast imaging report in the training set of breast imaging reports, extracting a region of text containing at least one focus word. In situations where a breast imaging report is fully or partially embodied as paper text, an OCR process may be implemented to electronically convert the paper text content within the report to machine-encoded text (i.e., digital text). The method may further include, for each breast imaging report in the training set of breast imaging reports, using a focus region search. The focus region search may identify targeted regions of the breast imaging report, e.g., regions containing focus words relevant to the plurality of breast density classes. In some aspects, step 510 may include extracting a region of text containing at least one focus word, where a relevance metric computation module (e.g., relevance metric computation module 120B) may perform the extracting.

The list of relevant focus words may be predetermined and may include a set of words identified by an entity familiar with the type of breast imaging report being analyzed. The selection of focus words may allow the method to be tailored to the type of reports being classified, such as breast imaging reports, and the data of interest within the reports being analyzed. For example, the focus words may be relevant to a breast density type. In this scenario, the at least one focus word may include, for example, dense, density, densities, heterogeneous, heterogeneously, scattered, fibroglandular, fat, fatty, extreme, extremely, moderate, mildly, largely, entirely, fatty replaced, average, and/or scattered areas of fibroglandular density. Some focus words may directly carry information that indicates an association with one of the breast density classes, while some focus words may carry information that indicates that the region of text around the focus word may include relevant information, even if such focus words are not themselves specific to a particular breast density class.

In the previous examples, fat, fatty, and entirely point to class A, scattered, fibroglandular, and scattered areas of fibroglandular density point to class B, heterogeneous and heterogeneously point to class C, and extreme and extremely point to class D. However, dense, density, densities, moderate, mildly, largely, fatty replaced, and average may indicate the presence of a text passage with information on breast density, even though these words themselves don't point to a specific class. Independent of the initial indication of a focus word, subsequent machine learning may be applied to classify a text region identified by the presence of focus words. For example, negated statements like "the breasts do not appear to be entirely fatty" and unrelated statements like "the image quality is extremely low" may be identified as containing focus words, while the final classification result is not indicated by the focus words. In some aspects, a passage or statement may not be "in focus" (i.e., the text passage is not relevant for classification purposes) despite containing one or more focus words. More particularly, machine learning techniques may be applied to identify a context of a passage (e.g., by examining the relationship between the focus words and the surrounding words and/or phrases in a passage) and to ultimately determine that the passage is contextually irrelevant to classification and should therefore not be considered as being in focus for a subsequent training or scoring task.

Using a focus region may be beneficial in breast imaging reports in which relevant information appears in a few isolated places in each breast imaging report. Isolating regions of text surrounding the focus words that are relevant to the relevant information contained in the breast imaging report may eliminate irrelevant text and strengthen the signal from the data.

At step 515, the method may include training a trained classifier (e.g., trained classifier 120) based on the extracted region of text containing at least one focus word. For example, the classifier extracts regions of text around the focus words in the training data and may train on those focus regions. The training may include steps 520-525, as described below.

At step 520, the method may include computing the training relevance metric for each breast imaging report in the training set of breast imaging reports, where the relevance metric computation module (e.g., relevance metric computation module 120B) may perform the computing. The training relevance metric may correspond to each term that appears in a set of breast imaging reports. Such terms may be provided by subject matter experts in the relevant field. In some aspects, the terms may be determined by unsupervised or supervised clustering of training breast imaging reports or regions in training breast imaging reports, which have been annotated by subject matter experts to contain relevant information. The terms may be characterized by a training relevance metric computed from frequency statistics, which capture how often a term may occur in text passages indicative of a breast density class, how often a term may occur in text passages that are not indicative of a breast density class, and what fraction of an input text carries relevant information. A training reference metric may be high if a term occurs frequently in text passages indicative of a breast density class, and rarely in text passages in input documents that are not indicative of a breast density class. For example, the training relevance metric may be computed as a training term frequency-inverse document frequency (tf-idf) vector that corresponds to each focus region for each breast imaging report. The relevance metric, e.g., tf-idf vector, allows the system to measure how relevant a breast imaging report is to a certain term. A breast imaging report that is highly relevant to a given term may be one in which the term appears frequently relative to the number of breast imaging reports that contain the term. Thus, to capture a breast imaging report's relevance overall, the method computes a vector of relevance metric scores, e.g., tf-idf scores, corresponding to each term that appears in the set of breast imaging reports.

The underlying assumption is that a breast imaging report that includes relevant information can be relevant to different terms to different extents. For example, a mammogram report describing different breast density types may be relevant to different terms to different extents. Based on this property, the system may approximate a training relevance metric signature, e.g., tf-idf signature, for each breast density class. A tf-idf signature may be a specific tf-idf vector, where the tf-idf signature may be computed by averaging the tf-idf vectors for all of the training breast imaging reports of a certain breast density class. Given a training set of mammogram reports with associated breast density classifications, the system may compute the relevance metric vector, e.g., tf-idf vector, for each breast imaging report.

At step 525, the method may include computing, for each breast density class in the plurality of breast density classes, an average of the training relevance metrics for all breast imaging reports of the same breast density class, where a relevance metric computation module (e.g., relevance metric computation module 120B) may perform the computing. The averaging of the training relevance metrics for all documents may be computed by taking all of the words in the regions of interest (those within some range of the focus words), where the regions of interest are accumulated for training examples in the same class, and then computing the result vector with regards to the relevance metric. At step 525, the classifier averages all of the training relevance metrics for all of the breast imaging reports of the same breast density class, resulting in a single average training relevance metric vector for each breast density class in the plurality of breast density classes. The single average training relevance metric for each breast density class in the plurality of breast density classes may be produced, or displayed, on a server display (e.g., display 115C) and/or a user device display (e.g., display 105A), or it may be stored in a server system memory (e.g., memory 115E), a server system database (e.g., database 115A), and/or a user device memory (e.g., memory 105C).

Another example of computing the average of the training relevance metric, such as a tf-idf vector, may be determined by selecting a certain number of the highest averages of the training relevance metric of breast imaging reports in the training set of breast imaging reports that belong to the same breast density class. For example, the five highest training relevance metric averages of the breast imaging reports of the same breast density class may be selected, added, and divided by five to determine the training relevance metric for the breast density class. In this example, the n highest training relevance metric averages of the documents of the same class may be selected, added, and divided by n to determine the training relevance metric for the class, wherein n is a number greater than zero and less than the number of documents in the training set of documents that belong to the same class. This process may be repeated for all of the breast density classes, resulting in an average training relevance metric for each breast density class.

If the training relevance metric is a tf-idf vector, for example, the relevance metric computation module (e.g., relevance metric computation module 1206) may compute the average tf-idf vector for each breast density class of the plurality of breast density classes. All of the tf-idf vectors for the same breast density class of all the breast imaging reports in the set of breast imaging reports may then be added and divided by the number of breast imaging reports in the set of breast imaging reports, resulting in the average tf-idf vector.

As discussed above in reference to FIG. 3, a trained classifier (e.g., trained classifier 120) may be trained to classify a breast imaging report by optimizing a set of hyperparameters using an iterative grid search algorithm based on a training set of breast imaging reports, e.g., by utilizing a trained machine-learning model, such as a machine-learning model trained according to one or more embodiments discussed above. The method may proceed as described in reference to FIG. 3.

The Machine-Learning Model Automatically Classifying a Breast Imaging Report

Figure 6:
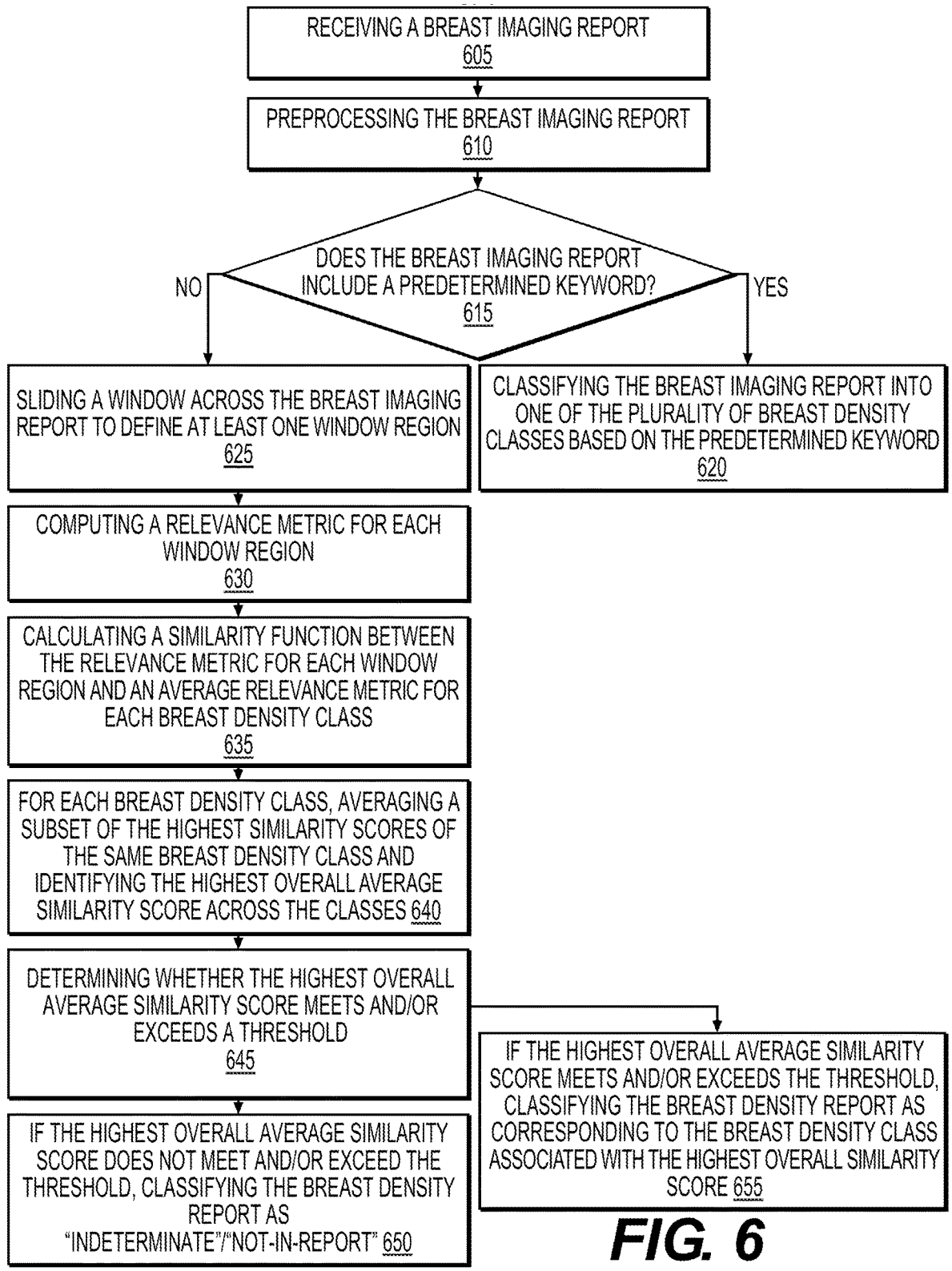
FIG. 6 depicts a flowchart of an exemplary method for automatically classifying a breast imaging report, according to one or more embodiments.

FIG. 6 illustrates an exemplary process for automatically extracting information from a breast imaging report to classify the breast imaging report, e.g., by utilizing a trained machine-learning model, such as a machine-learning model trained according to one or more embodiments discussed above.

At step 605, the method may include receiving a breast imaging report, where the breast imaging report contains textual information, such as doctor's notes or an imaging read. In some aspects, the breast imaging report may contain digital text (e.g., typed text, etc.), paper text (e.g., printed text, handwritten text, etc.), or a combination thereof. The breast imaging report may be a free text breast imaging report, for example, a mammogram report. The breast imaging report may be received by a user device (e.g., user device 105) and sent via a network (e.g., network 101) to a server system (e.g., server system 115), which then receives the breast imaging report. The breast imaging report may also be received directly by the server system (e.g., server system 115). The server system may store the breast imaging report in a database (e.g., database 115A) or in a memory (e.g., memory 115E).

At step 610, the method may include preprocessing the breast imaging report, where the preprocessing may be performed by a preprocessing module (e.g., preprocessing module 120A). The preprocessing may include at least one of: formatting the document, removing at least one stopword from the breast imaging report, and/or stemming at least one word in the breast imaging report, as described above in reference to FIG. 4.

In situations where a breast imaging report is fully or partially embodied as paper text, an OCR process may be implemented to electronically convert the paper text content within the report to machine-encoded text (i.e., digital text), which may allow stopword removal and/or stemming to more easily be performed.

The method may further include determining whether the breast imaging report includes at least one predetermined keyword (e.g., individual key words or key phrases), shown in step 615. As discussed above, for example, the at least one predetermined keyword may include at least one of: "the breasts are almost entirely fat" (Class A), "the rest of the breasts are mildly dense" (Class B), "there are scattered densities throughout the breast" (Class B), "the breast tissue is dense" (Class C), "the breasts are heterogeneously dense, which may obscure small masses" (Class C), and/or "the right breast is very dense" (Class D).

If the breast imaging report is determined to include at least one predetermined keyword, the breast imaging report may be classified into one of the plurality of breast density classes based on the predetermined keyword, shown in step 620. A keyword may be so directly related to a breast density class of the plurality of breast density classes that if the classifier finds the keyword in the breast imaging report, it can rely on the presence of the keyword in the breast imaging report to classify the breast imaging report and bypasses the rest of method steps 625 through 655. For example, if the breast imaging report includes the predetermined keyword "the breasts are almost entirely fat," or "Class A," then the breast imaging report may be automatically classified as a fatty class (Class A). As a result, by directly classifying the breast imaging report using the keyword, the rest of the method steps may be omitted. For example, steps 625 through 655 of the method are not performed if the breast imaging report includes a predetermined keyword, since the keyword will instead be used to classify the breast imaging report.

The list of relevant keywords may be predetermined and may include a set of words identified by an entity familiar with the type of breast imaging report being analyzed. The term "keyword," as used herein, may refer to a single word, a short sequence of words, or a phrase. Different keywords may be associated with different breast density classes of the plurality of breast density classes, so that the trained classifier (e.g., trained classifier 120) may identify the presence of a keyword and then classify the breast imaging report as associated with the breast density class with which the keyword is associated. The selection of keywords may allow the method to be tailored to the type of breast imaging reports and data within the breast imaging reports being analyzed.

If the breast imaging report does not contain a predetermined keyword, the method may proceed to step 625, where the method may include applying a sliding window search to slide a window across the breast imaging report to define at least one window region, where the trained classifier (e.g., trained classifier 120) may perform the sliding window search, as described in reference to FIG. 4.

At step 630, the method may include computing a relevance metric for each window region, where the relevance metric computation module (e.g., relevance metric computation module 120B) may perform the computing, as described above.

At step 635, the method may include calculating a similarity function or distance function between the relevance metric for each window region and an average relevance metric for each breast density class, where the similarity score module (e.g., similarity score module 120C) may perform the calculating. The calculated similarity or distance function for each breast density class may be assigned as the similarity score for each breast density class's window region. For example, the relevance metric for each window may include a tf-idf vector, and the average relevance metric may be an average tf-idf vector for each breast density class. As a result, a similarity or distance function, such as a cosine similarity, city block distance, Cartesian distance, and/or Mahalanobis distance, may be calculated between the tf-idf vector for each window and the average tf-idf vector for each breast density class. This means that each window region has a similarity score for each breast density class.

At step 640, the method may include computing an overall similarity score for the breast imaging report, as described above.

At step 645, the method may include determining whether the highest overall similarity score meets and/or exceeds a threshold, where the document classification module (e.g., document classification module 120D) may perform the determining, as described above in reference to FIG. 4.

If the difference does not meet or exceed the threshold, then the breast imaging report may proceed to step for 650, where the breast imaging report may be classified as corresponding to an indeterminate class. If the overall similarity score does meet or exceed the threshold, then at step 655, the method may include classifying the breast imaging report as corresponding to the breast density class with which the highest overall similarity score is associated with, where the document classification module (e.g., document classification module 120D) may perform the classifying.

Figure 7:
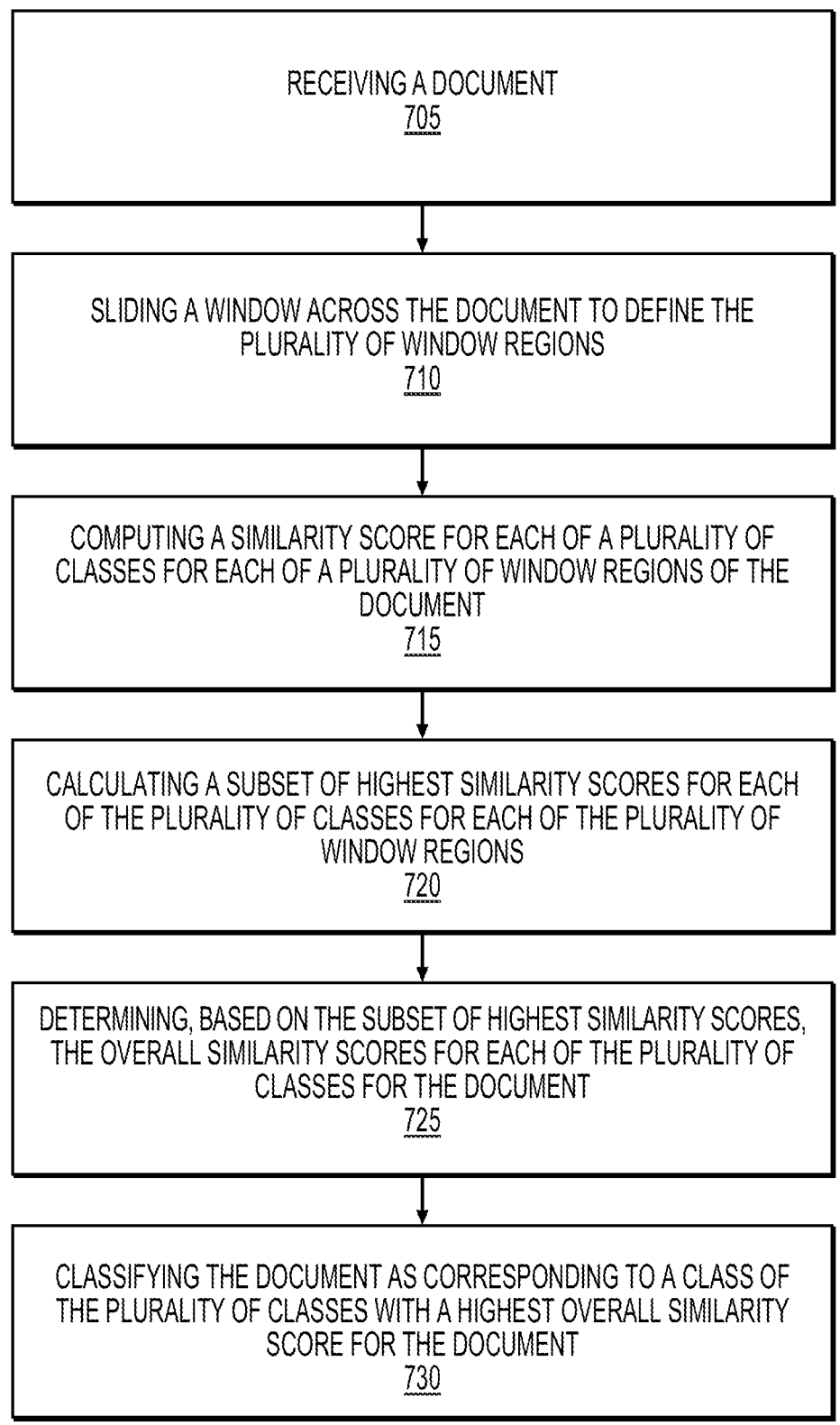
FIG. 7 depicts a flowchart of an exemplary method for automatically classifying a document, according to one or more embodiments.

FIG. 7 illustrates a general overview of an exemplary process for automatically extracting information from a document to classify the document, e.g., by utilizing a trained machine-learning model, such as a machine-learning model trained according to one or more embodiments discussed above.

At step 705, the method may include receiving a dataset, e.g., a document, where the document may contain textual information. The method may include classifying the document into one of a plurality of classes, where the classifying may include steps 710-730.

At step 710, may include sliding a window across the textual information to define the plurality of window regions. The method may then include computing a similarity score for each of the plurality of classes for each of a plurality of window regions of the document, as shown in step 715.

At step 720, the method may include calculating a subset of highest similarity scores for each of the plurality of classes for each of the plurality of window regions.

At step 725, the method may include determining, based on the subset of highest similarity scores, overall similarity scores for each of the plurality of classes for the document.

At step 730, the method may include classifying the document as corresponding to a class of the plurality of classes with a highest overall similarity score for the document.

Training a Machine-Learning Model for Multiple Classifications

Referring back to FIG. 5, in some aspects, a training method may include receiving a training set of breast imaging reports that are already associated with a plurality of breast density classes. A given report of the one or more training reports may be associated with a plurality of classes. The plurality of breast density classes may include, as discussed above, at least one of a fatty class (Class A), a scattered fibroglandular density class (Class B), a heterogeneously dense class (Class C), an extremely dense class (Class D), and an indeterminate class. In some aspects, a single report may contain information for both the left breast and the right breast, and the information for the left breast and the right breast may be associated with different classes of the plurality of breast density classes. For example, in one report, the left breast may be described with language associated with a first of the plurality of classes, and the right breast may be described with language associated with a second of the plurality of classes.

To handle a report that contains information relevant to two different classes, the plurality of classes may further include a 'multiple class.' The trained classifier may classify a report in the multiple class if the report contains information, for example, about both the left breast and the right breast, and the left breast and the right breast language would lead to a classification of the left breast information into a class that is different from the right breast information.

In other aspects, however, the trained classifier may classify the report in both of the classes with which the left breast and the right breast would be associated, instead of classifying the document as falling into a multiple class. In a variation of this embodiment, the plurality of breast density classes may include a fatty class (Class A) for the right breast, a scattered fibroglandular density class (Class B) for the right breast, a heterogeneously dense class (Class C) for the right breast, an extremely dense class (Class D) for the right breast, an indeterminate class for the right breast, a fatty class (Class A) for the left breast, a scattered fibroglandular density class (Class B) for the left breast, a heterogeneously dense class (Class C) for the left breast, an extremely dense class (Class D) for the left breast, and an indeterminate class for the left breast. The classifications for the left breast and the classifications for the right breast may be the same or different. As a result, an individual report may be able to be classified as including information relevant to two different classes—one class for the right breast and one class for the left breast. Although indeterminate classes are listed as separate classes for the right breast and the left breast above, it is also possible that one indeterminate class is included in the plurality of classes.

As discussed above, a server system (e.g., server system 115) may receive a set of breast imaging reports, and the server system (e.g., server system 115) may store the set of breast imaging reports in a database (e.g., database 115A) or in a memory (e.g., memory 115E). For example, the set of breast imaging reports received may include reports that include information about the right breast or left breast, reports that include information about both the left breast and the right breast, and/or reports that include historical information about the left breast and/or the right breast. For example, in regards to historical information, the set of breast imaging reports may include information about breast density as determined from comparing a current mammogram to the breast density that was determined based on previous mammograms. As a result, breast density changes may be captured over time. In other aspects, the set of breast imaging reports may further compare the breast density of the current mammogram to the breast density determined using different imaging devices or if different densities were identified by different image readers from the same mammogram.

At step 510, the method may include, for each breast imaging report in the training set of breast imaging reports, using a focus region search. The focus region search may identify targeted regions of the breast imaging report, e.g., regions containing focus words relevant to the plurality of breast density classes. In some aspects, the focus words in this embodiment may include those listed above, as well as indicator focus words, such as left, right, left breast, right breast, breast A, and/or breast B. The presence of multiple indicator focus words, each associated with regular focus words, may signal that the report may include information relevant to multiple classes within the report, e.g., a class associated with the right breast, and a class associated with the left breast. If indicator focus words are identified, then the method may proceed as described above, except that the training may separately consider focus words associated with each indicator focus word identified within a document. In other words, the training may proceed for each class associated with focus words for each indicator.

At step 520, the method may include computing the training relevance metric for each breast imaging report in the training set of breast imaging reports, where the relevance metric computation module (e.g., relevance metric computation module 120B) may perform the computing. The training relevance metric may correspond to each term that appears in a set of breast imaging reports. For example, the training relevance metric may be computed as a training term frequency-inverse document frequency (tf-idf) vector that corresponds to each focus region for each breast imaging report. The relevance metric, e.g., tf-idf vector, allows the system to measure how relevant a breast imaging report is to a certain term. A breast imaging report that is highly relevant to a given term is one in which the term appears frequently relative to the number of breast imaging reports that contain the term. Thus, to capture a breast imaging report's relevance overall, the method computes a vector of relevance metric scores, e.g., tf-idf scores, corresponding to each term that appears in the set of breast imaging reports.

At step 525, the method may include computing, for each breast density class in the plurality of breast density classes, an average of the training relevance metrics for all breast imaging reports of the same breast density class, where a relevance metric computation module (e.g., relevance metric computation module 120B) may perform the computing. At step 525, the classifier averages all of the training relevance metrics for all of the breast imaging reports of the same breast density class, and/or all of the portions of breast imaging reports of the same breast density class (if the report has left and right breast density information relevant to two different classes, for example), resulting in a single average training relevance metric vector for each breast density class in the plurality of breast density classes. The method may proceed in a similar manner as described above in reference to FIG. 5.

Automatically Classifying a Breast Imaging Report into Multiple Classifications

Referring back to FIG. 6, the figure illustrates an exemplary process for automatically extracting information from a breast imaging report to classify the breast imaging report, e.g., by utilizing a trained machine-learning model, such as a machine-learning model trained according to one or more embodiments discussed above. For the detection of multiple information—for example right and left breast, or current imaging studies compared to previous imaging studies—the classifier may also be trained with training data and focus words that indicate that a current focus region contains information for the left or right breast and/or current or previous imaging studies. Such training may be performed in parallel to, and independent of, training and classifying a focus region as indicating one of the breast density classes.

As discussed above, step 615 of FIG. 6 may include performing a keyword analysis to determine whether the breast imaging report includes at least one predetermined keyword (e.g., individual key words or key phrases). For example, the at least one predetermined keyword may include at least one of: "the breasts are almost entirely fat" (Class A), "the rest of the breasts are mildly dense" (Class B), "there are scattered densities throughout the breast" (Class B), "the breast tissue is dense" (Class C), "the breasts are heterogeneously dense, which may obscure small masses" (Class C), and/or "the right breast is very dense" (Class D).

If the breast imaging report is determined to include at least one predetermined keyword, the breast imaging report may be classified into one of the plurality of breast density classes based on the predetermined keyword, shown in step 620. Such predetermined keywords may include right, left, ipsilateral, contralateral, current, recent, previous, prior, and history. In the case of a breast imaging report that includes multiple keywords that are associated with different classes, as well as indicator focus words, then the report may be classified into the multiple class, or may be classified as both classes that are associated with the identified keywords. As a result, by directly classifying the breast imaging report using the keywords, the rest of the method steps may be omitted. For example, steps 625 through 655 of the method are not performed if the breast imaging report includes one or more predetermined keywords, since the keywords will instead be used to classify the breast imaging report.

If the breast imaging report does not contain one or more predetermined keywords, the method may proceed to step 625, where the method may include applying a sliding window search to slide a window across the breast imaging report to define at least one window region, where the trained classifier (e.g., trained classifier 120) may perform the sliding window search.

At step 630, the method may include computing a relevance metric for each window region, where the relevance metric computation module (e.g., relevance metric computation module 120B) may perform the computing. If there is more than one window region, the relevance metric may be computed for each window region. For example, the relevance metric may be computed as a tf-idf vector that corresponds to each window region.

At step 635, the method may include calculating a similarity function or distance function between the relevance metric for each window region and an average relevance metric for each breast density class, where the similarity score module (e.g., similarity score module 120C) may perform the calculating. The calculated similarity function for each breast density class may be assigned as the similarity score for each breast density class's window region. For example, the relevance metric for each window may include a tf-idf vector, and the average relevance metric may be an average tf-idf vector for each breast density class. As a result, a similarity function or distance function, such as a cosine similarity, city block distance, Cartesian distance, and/or Mahalanobis distance, may be calculated between the tf-idf vector for each window and the average tf-idf vector for each breast density class. This means that each window region has a similarity score for each breast density class.

At step 640, the method may include computing an overall similarity score for the breast imaging report. Trained classifier 120 (e.g., document classification module 120D) may select the highest average of similarity scores across all of the breast density classes as the overall similarity score for the breast imaging report. For example, the document classification module (e.g., document classification module 120D) may compare all of the highest averages of similarity scores for all of the breast density classes to determine which breast density class has the highest average similarity score, and the highest similarity score may be assigned to the breast imaging report as the overall average similarity score. In embodiments in which a report may contain information relevant to more than one class and may be classified as multiple classes (e.g., when information about the right breast and the left breast is included), the highest and second-highest similarity scores may be assigned to the breast imaging report as the highest overall average similarity scores, or the highest similarity scores associated with each relevant keyword, like right, left, ipsilateral, contralateral, current, recent, previous, prior, and history may be assigned to the breast imaging report as the highest overall average similarity scores.

At step 645, the method may include determining whether the highest overall average similarity scores meet and/or exceed a threshold, where the document classification module (e.g., document classification module 120D) may perform the determining. As discussed above, a hyperparameter may be used to indicate the threshold value, where not meeting or exceeding the threshold value results in an indeterminate classification. If a report contains information about two separate classes that are different from one another, if the highest overall average and the second highest overall average meet and/or exceed the threshold, then the breast imaging report may be classified as belonging to the breast density class of the highest and second-highest overall average similarity scores (i.e., as belonging to two classes), whether or not the highest and second-highest overall average similarity scores are associated with neighboring classes. Alternatively, if the highest and second-highest overall average meet and/or exceed the threshold, then the report may be assigned to the multiple class, indicating that the report may contain multiple classes. If the highest and second-highest overall average do not meet and/or exceed the threshold, then the report may be assigned to the indeterminate class.

Additionally, the multiple classes embodiment is not limited to left and right breasts in mammogram reports, but rather the multiple classes category of classes may be applied to any type of document that includes information regarding multiple aspects that could be assigned to two different classes within the same report.

Application for Cancer Detection, Monitoring, and Treatment

In some embodiments, the methods, systems and/or trained classifier of the present disclosure can be used to detect the presence (or absence) of cancer, monitor cancer progression or recurrence, monitor therapeutic response or effectiveness, determine a presence or monitor minimum residual disease (MRD), or any combination thereof. In some embodiments, the systems and/or trained classifier may be used to identify the tissue or origin for a cancer. For instance, the systems and/or trained classifier may be used to identify a cancer as of any of the following cancer types: head and neck cancer, liver/bile duct cancer, upper GI cancer, pancreatic/gallbladder cancer; colorectal cancer, ovarian cancer, lung cancer, multiple myeloma, lymphoid neoplasms, melanoma, sarcoma, breast cancer, and/or uterine cancer. In some embodiments, a test report can be generated to provide a patient with their test results, including, for example, a probability score that the patient has a disease state (e.g., cancer), a type of disease (e.g., a type of cancer), and/or a disease tissue of origin (e.g., a cancer tissue of origin). In some embodiments, the methods and/or trained classifier of the present disclosure are used to detect the presence or absence of cancer in a subject suspected of having cancer. According to aspects of the disclosure, the methods and systems of the present disclosure can be trained to detect or classify multiple cancer indications. For example, the methods, systems and trained classifier of the present disclosure can be used to detect the presence of one or more, two or more, three or more, five or more, or ten or more different types of cancer. In some embodiments, the cancer is one or more of head and neck cancer, liver/bile duct cancer, upper GI cancer, pancreatic/gallbladder cancer; colorectal cancer, ovarian cancer, lung cancer, multiple myeloma, lymphoid neoplasms, melanoma, sarcoma, breast cancer, and/or uterine cancer.

The document can be obtained from a cancer patient over any set of time points and analyzed in accordance with the methods of the disclosure to monitor a cancer state in the patient. In some embodiments, a first time point may be before a cancer treatment (e.g., before a resection surgery or a therapeutic intervention), and the second time point may be after a cancer treatment (e.g., after a resection surgery or therapeutic intervention), and the method may be utilized to monitor the effectiveness of the treatment. In other embodiments, both the first and second time points may be before a cancer treatment (e.g., before a resection surgery or a therapeutic intervention). In still other embodiments, both the first and the second time points may be after a cancer treatment (e.g., before a resection surgery or a therapeutic intervention) and the method may be used to monitor the effectiveness of the treatment or loss of effectiveness of the treatment. In still other embodiments, documents may be obtained from a cancer patient at a first and second time point and analyzed (e.g., to monitor cancer progression, to determine if a cancer is in remission (e.g., after treatment), to monitor or detect residual disease or recurrence of disease, or to monitor treatment (e.g., therapeutic) efficacy).

In some embodiments, the first and second time points may be separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, documents can be obtained from the patient at least once every 3 months, at least once every 6 months, at least once a year, at least once every 2 years, at least once every 3 years, at least once every 4 years, or at least once every 5 years.

In still another embodiment, information obtained from any method described herein can be used to make or influence a clinical decision (e.g., diagnosis of cancer, treatment selection, assessment of treatment effectiveness, etc.). For example, in one embodiment, a physician can prescribe an appropriate treatment (e.g., a resection surgery, radiation therapy, chemotherapy, and/or immunotherapy) based on the classification of the documents. In some embodiments, information such as the classification of the documents can be provided as a readout to a physician or subject. In some embodiments, classification of the document can indicate the effectiveness of a cancer treatment.

In some embodiments, the treatment is one or more cancer therapeutic agents selected from the group including a chemotherapy agent, a targeted cancer therapy agent, a differentiating therapy agent, a hormone therapy agent, and/or an immunotherapy agent. For example, the treatment can be one or more chemotherapy agents selected from the group including alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment can be one or more targeted cancer therapy agents selected from the group including signal transduction inhibitors (e.g., tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment can be one or more differentiating therapy agents including retinoids, such as tretinoin, alitretinoin and bexarotene. In some embodiments, the treatment can be one or more hormone therapy agents selected from the group including anti-estrogens, aromatase inhibitors, progestins, estrogens, anti-androgens, and GnRH agonists or analogs. In one embodiment, the treatment can be one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). The appropriate cancer therapeutic agent can be selected based on characteristics such as the type of tumor, cancer stage, previous exposure to cancer treatment or therapeutic agent, and other characteristics of the cancer.

EXAMPLE 1

Training Results

An example model was formed to test one or more of the embodiments described herein. In this first example, a classifier was trained on a dataset of 434 mammogram reports, which had been labeled with true classification values by a physician in the relevant field. Table 1 summarizes the true classification breakdown of the dataset:

TABLE 1

|  | a | b | c | d | not |
|---|---|---|---|---|---|
| Count | 36 | 131 | 215 | 42 | 10 |
| Proportion | 0.0829 | 0.3018 | 0.4954 | 0.0968 | 0.0230 |

Based on the training data, the optimizer selected the following hyperparameters for the classifier:
a. Focus region size: 3
b. Sliding window size: 2
c. Number of similarity scores to average: 1
d. Indeterminate similarity threshold: 0.27

In the dataset, for the indeterminate similarity threshold, similarity scores range from zero to one, inclusive. Notably, the optimizer converged on small values for the focus region size and the sliding window size. This suggests that the focus words were well-chosen, since the information relevant to breast density classification occurs within only a few words around them. The optimizer also chose to use only the highest similarity score for each document. This suggests that the relevant information tends to only occur at a single place in the documents used for this example model.

If it is possible, however, that depending on the type of documents being analyzed and classified, even well-chosen focus words may result in the optimizer selecting larger values, for example, if the relevant information tends to be described using more words, is more spread out throughout the document, and/or reoccurs throughout the document.

EXAMPLE 2

Evaluation Results

In this example, the test dataset had 590 mammogram reports, each of which had been labeled with the true classification. The authors in this example were blinded to the test data while developing the system. The mammogram reports came from several different study sites to ensure that they gave an accurate representation. Table 2, below, summarizes the true classification breakdown of the test dataset:

TABLE 2

|  | a | b | c | d | not |
|---|---|---|---|---|---|
| Count | 52 | 250 | 247 | 35 | 6 |
| Proportion | 0.0881 | 0.4237 | 0.4186 | 0.0593 | 0.0102 |

Table 3 shows the distribution of breast density classes in the test set and in the general population. This table demonstrates that the proportion of each class in the test dataset roughly lines up with its proportion in the general population. This allowed the authors to estimate the classifier's true accuracy.

TABLE 3

|  | a | b | c | d |
|---|---|---|---|---|
| Test Set Proportion | 0.09 | 0.43 | 0.42 | 0.06 |
| General Population Proportion[6] | 0.05 | 0.45 | 0.45 | 0.05 |

Figure 8:
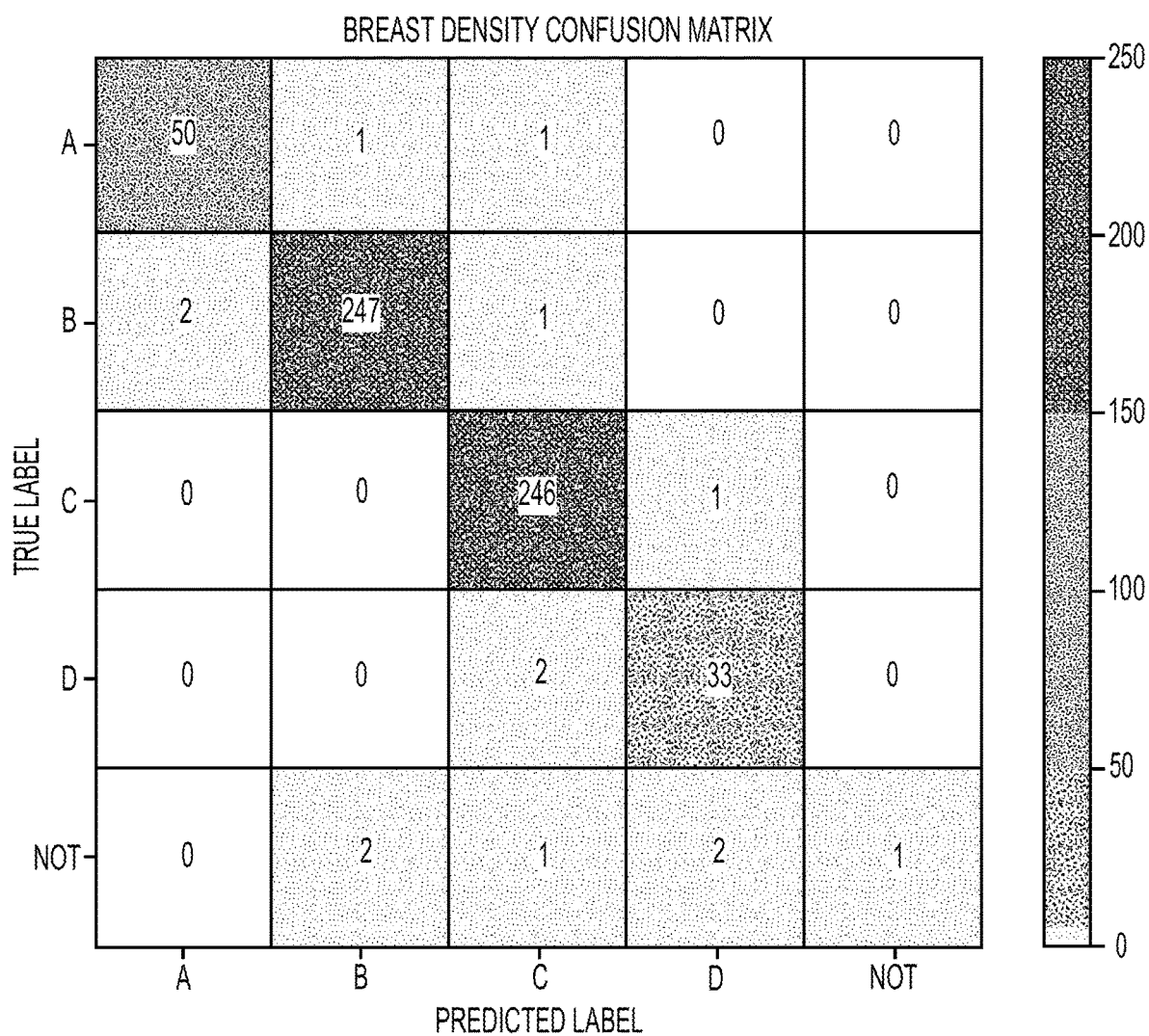
FIG. 8 depicts a sample of classification results for an example set of test cases, according to one or more embodiments.

The system correctly classified 577 out of 590 reports, for an accuracy of 97.80%. FIG. 8 further displays the classification results. As can be observed from the confusion matrix, for Class A, the system correctly classified 50 out of 52 reports, for Class B, the system correctly classified 247 out of 250 reports, for Class C, the system correctly classified 246 out of 247 reports, and for Class D, the system correctly classified 33 out of 35 reports. The system classified 6 reports as being in an indeterminate class, or "not."

This example demonstrates the efficacy of the test classifier. Additionally, even the classifier's incorrect predictions demonstrated that it accurately captured the structure of the data. Because breast density is on a spectrum from less dense to more dense, it can be expected that the language used to describe the four breast density classes would fall along a spectrum as well. For example, descriptions of Class A would likely be similar to descriptions of Class B, and less similar to descriptions of Classes C and D. The dataset matches this assumption. Indeed, of the eight cases where a report with breast density information was misclassified, seven of them were classified as a direct neighbor of the report's true class.

It should be understood that embodiments in this disclosure are exemplary only, and that other embodiments may include various combinations of features from other embodiments, as well as additional or fewer features. For example, while some of the embodiments above pertain to automated extraction of document information, any suitable activity may be used.

In general, any process or operation discussed in this disclosure that is understood to be computer-implementable, such as the processes illustrated in FIGS. 2-7, may be performed by one or more processors of a computer system, such any of the systems or devices in the environment 100 of FIG. 1, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 1. One or more processors of a computer system may be included in a single computing device or distributed among a plurality of computing devices. A memory of the computer system may include the respective memory of each computing device of the plurality of computing devices.

Figure 9:
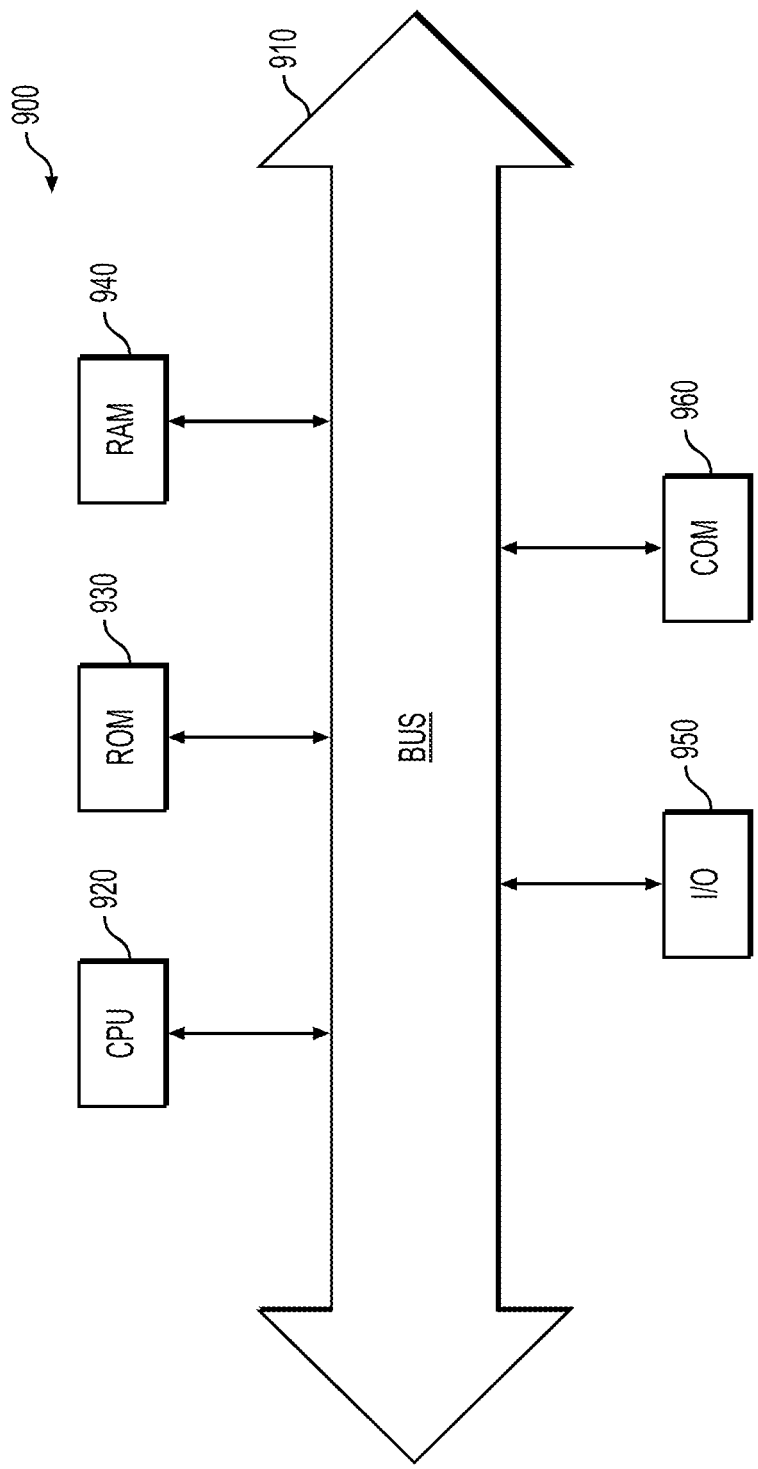
FIG. 9 depicts an example of a computing device, according to one or more embodiments.

FIG. 9 is a simplified functional block diagram of a computer 900 that may be configured as a device for executing the methods of FIGS. 2-7, according to exemplary embodiments of the present disclosure. For example, device 900 may include a central processing unit (CPU) 920. CPU 920 may be any type of processor device including, for example, any type of special purpose or a general-purpose microprocessor device. As will be appreciated by persons skilled in the relevant art, CPU 920 also may be a single processor in a multi-core/multiprocessor system, such system operating alone, or in a cluster of computing devices operating in a cluster or server farm. CPU 920 may be connected to a data communication infrastructure 910, for example, a bus, message queue, network, or multi-core message-passing scheme.

Device 900 also may include a main memory 940, for example, random access memory (RAM), and also may include a secondary memory 930. Secondary memory 930, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include other similar means for allowing computer programs or other instructions to be loaded into device 900. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 900 and external devices. Communications interface 960 may include a modem, a network interface (such as an Ethernet card), a communications port, a PCMCIA slot and card, or the like. Software and data transferred via communications interface 960 may be in the form of signals, which may be electronic, electromagnetic, optical, or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 900 also may include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

The systems, apparatuses, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these apparatuses, devices, systems, or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified by context, any explicit or implicit ordering of steps performed in the execution of a method does not imply that those steps must be performed in the order presented but instead may be performed in a different order or in parallel.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the disclosed methods, devices, and systems are described with exemplary reference to transmitting data, it should be appreciated that the disclosed embodiments may be applicable to any environment, such as a desktop or laptop computer, an automobile entertainment system, a home entertainment system, etc. Also, the disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for extracting information from a dataset, comprising:
    receiving, at an information handling device, a dataset;
    extracting, via optical character recognition implemented by a processor of the information handling device, textual information associated with the dataset; and
    classifying the dataset into one of a plurality of classes, the classifying further comprising:
        computing a similarity score for each of the plurality of classes for each of a plurality of window regions of the dataset, the computing further comprising:
            sliding a window across the textual information to define the plurality of window regions, and for each of the plurality of window regions:
                computing a relevance metric for the window region; and
                calculating the similarity score for each of the plurality of classes by calculating a similarity function between the relevance metric for the window region and an average relevance metric for each of the plurality of classes;
        determining, based on a subset of highest similarity scores computed for each of the plurality of classes for each of the plurality of window regions, overall similarity scores for each of the plurality of classes for the dataset; and
        classifying the dataset as corresponding to a class of the plurality of classes with a highest overall similarity score for the dataset.

2. The computer-implemented method of claim 1, wherein the subset of highest similarity scores for each of the plurality of classes for each of the plurality of window regions are averaged to determine the overall similarity scores for each of the plurality of classes for the dataset.

3. The computer-implemented method of claim 1, wherein the subset of highest similarity scores comprises one similarity score.

4. The computer-implemented method of claim 1, wherein the similarity function is a cosine similarity.

5. The computer-implemented method of claim 1, wherein computing the relevance metric includes computing a frequency-inverse dataset frequency (tf-idf) vector for the window region.

6. The computer-implemented method of claim 1, the classifying further comprising:
    determining whether the highest overall similarity score for the dataset meets or exceeds a threshold; and
    if the highest overall similarity score for the dataset does not meet or exceed the threshold, classifying the dataset as corresponding to an indeterminate class.

7. The computer-implemented method of claim 1, wherein the dataset is a medical report.

8. The computer-implemented method of claim 7, wherein the dataset is a mammography report, wherein the textual information includes breast density information, and wherein the plurality of classes comprises at least one of: a fatty class, a scattered fibroglandular density class, a heterogeneously dense class, an extremely dense class, an indeterminate class, or a multiple class.

9. The computer-implemented method of claim 1, further comprising:
    preprocessing the dataset, the preprocessing including at least one of: removing at least one stopword from the dataset or stemming at least one word in the dataset.

10. The computer-implemented method of claim 9, wherein the at least one stopword includes at least one of: it, what, is, are, the, a, an, and/or those.

11. The computer-implemented method of claim 1, further comprising:
    determining whether the dataset includes at least one predetermined keyword; and
    wherein if the dataset is determined to include the at least one predetermined keyword, classifying the dataset into a class of the plurality of classes comprises only determining the class of the plurality of classes based on the at least one predetermined keyword, and
    wherein the computing the similarity score for each of the plurality of classes for each of the plurality of window regions of the dataset, the determining the overall similarity scores for the dataset, and the classifying the dataset as corresponding to the class of the plurality of classes with a highest overall similarity score steps of the method of claim 1 are not performed.

12. The computer-implemented method of claim 11, wherein the at least one predetermined keyword comprises at least one of: right, left, ipsilateral, contralateral, current, recent, previous, prior, history, "the breasts are almost entirely fat," "the rest of the breasts are mildly dense," "there are scattered densities throughout the breast," "the breast tissue is dense," "the breasts are heterogeneously dense, which may obscure small masses," and/or "the right breast is very dense".

13. The computer-implemented method of claim 1, wherein a trained classifier performs the classifying the dataset into one of the plurality of classes.

14. The computer-implemented method of claim 13, wherein the trained classifier is trained on a training set of datasets that are each already associated with a class of the plurality of classes, the training comprising:
computing a training relevance metric for each dataset of the training set of datasets; and
averaging the training relevance metric for all datasets of the training set that are associated with a same class of the plurality of classes to produce the average training relevance metric corresponding to each class of the plurality of classes.

15. The computer-implemented method of claim 14, wherein the training set of datasets comprises a set of mammogram reports, wherein the associated class comprises at least one of: a fatty class, a scattered fibroglandular density class, a heterogeneously dense class, an extremely dense class, an indeterminate class, or a multiple class.

16. The computer-implemented method of claim 14, the training further comprising:
for each dataset of the training set of datasets, extracting a region of text containing at least one focus word; and
training the trained classifier based on the region of text.

17. The computer-implemented method of claim 16, wherein the at least one focus word comprises at least one of: dense, density, densities, heterogeneous, heterogeneously, scattered, fibroglandular, fat, fatty, extreme, extremely, moderate, mildly, largely, entirely, fatty replaced, average, and/or scattered areas of fibroglandular density.

18. The computer-implemented method of claim 13, wherein the trained classifier comprises a set of hyperparameters, the set of hyperparameters including at least one of: a size of each sliding window region, a size of a focus region around a focus word, a number of highest similarity scores in the subset on which to base the overall similarity scores for the dataset, and a threshold.

19. The computer-implemented method of claim 18, wherein the threshold indicates a minimum threshold similarity score.

20. The computer-implemented method of claim 14, wherein the training further comprises optimizing a set of hyperparameters using an iterative grid search algorithm based on the training set of datasets.

21. The computer-implemented method of claim 20, wherein the optimizing further comprises:
selecting, by an optimizer, a value for the set of hyperparameters;
calculating, by the optimizer, an accuracy of the trained classifier utilizing the set of hyperparameters; and
selecting, by the optimizer, an optimized value for the set of hyperparameters.

22. A computer system for extracting information from a dataset, the computer system comprising:
at least one memory storing instructions; and
at least one processor configured to execute the instructions to perform operations comprising:
access the at least one memory and execute processor-readable instructions, which when executed by the at least one processor configures the at least one processor to perform a plurality of functions, including functions for:
receiving, at an information handling device associated with the computer system, the dataset;
extracting, via optical character recognition implemented by the at least one processor, textual information associated with the dataset; and
classifying the dataset into one of a plurality of classes, the classifying further comprising:
computing a similarity score for each of the plurality of classes for each of a plurality of window regions of the dataset, the computing further comprising:
sliding a window across the textual information to define the plurality of window regions, and for each of the plurality of window regions:
computing a relevance metric for the window region; and
calculating the similarity score for each of the plurality of classes by calculating a similarity function between the relevance metric for the window region and an average relevance metric for each of the plurality of classes;
determining, based on a subset of highest similarity scores computed for each of the plurality of classes for each of the plurality of window regions, overall similarity scores for each of the plurality of classes for the dataset; and
classifying the dataset as corresponding to a class of the plurality of classes with a highest overall similarity score for the dataset.

23. A non-transitory computer-readable medium storing instructions that, when executed by a processor, cause the processor to perform operations for extracting information from a dataset, the operations comprising:
receiving the dataset;
extracting, via optical character recognition, textual information associated with the dataset; and
classifying the dataset into one of a plurality of classes, the classifying further comprising:
computing a similarity score for each of the plurality of classes for each of a plurality of window regions of the dataset, the computing further comprising:
sliding a window across the textual information to define the plurality of window regions, and for each of the plurality of window regions:
computing a relevance metric for the window region; and
calculating the similarity score for each of the plurality of classes by calculating a similarity function between the relevance metric for the window region and an average relevance metric for each of the plurality of classes;
determining, based on a subset of highest similarity scores computed for each of the plurality of classes for each of the plurality of window regions, overall similarity scores for each of the plurality of classes for the dataset; and
classifying the dataset as corresponding to a class of the plurality of classes with a highest overall similarity score for the dataset.

24. A computer-implemented method for extracting information from a dataset, comprising:
receiving, at an information handling device, the dataset;

extracting, via optical character recognition implemented by a processor of the information handling device, textual information associated with the dataset; and classifying the dataset into one of a plurality of classes, the classifying further comprising:

computing a similarity score for each of the plurality of classes for each of a plurality of window regions of the dataset, wherein the computing includes sliding a window across the textual information to define the plurality of window regions;

determining, based on a subset of highest similarity scores, overall similarity scores for each of the plurality of classes for the dataset; and classifying the dataset as corresponding to a class of the plurality of classes with a highest overall similarity score for the dataset.

\* \* \* \* \*